(12) United States Patent
Miyamoto et al.

(10) Patent No.: US 6,489,336 B2
(45) Date of Patent: Dec. 3, 2002

(54) NITROGEN-CONTAINING TRICYCLIC COMPOUNDS AND DRUGS CONTAINING THE SAME

(75) Inventors: Mitsuaki Miyamoto, Ibaraki (JP); Tatsuya Yoshiuchi, Ibaraki (JP); Keizo Sato, Ibaraki (JP); Makoto Kaino, Ibaraki (JP); Masayuki Tanaka, Ibaraki (JP); Motohiro Soejima, Ibaraki (JP); Katsuhiro Moriya, Ibaraki (JP); Yoshinori Sakuma, Ibaraki (JP); Koji Yamada, Ibaraki (JP); Kokichi Harada, Ibaraki (JP); Yukio Nishizawa, Ibaraki (JP); Seiichi Kobayashi, Ibaraki (JP); Makoto Okita, Ibaraki (JP); Koichi Katayama, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/985,416

(22) Filed: Nov. 2, 2001

(65) Prior Publication Data

US 2002/0103189 A1 Aug. 1, 2002

Related U.S. Application Data

(62) Division of application No. 09/125,451, filed as application No. PCT/JP97/00789 on Mar. 13, 1997, now Pat. No. 6,333,322.

(30) Foreign Application Priority Data

Mar. 13, 1996 (JP) .................................... 8-55628

(51) Int. Cl.[7] ..................... A61K 31/473; C07D 219/08
(52) U.S. Cl. ...................... 514/297; 546/105; 546/106; 546/103; 546/102
(58) Field of Search ................... 514/297; 546/105, 546/106, 102, 103

(56) References Cited

U.S. PATENT DOCUMENTS

| | | | |
|---|---|---|---|
| 3,449,334 A | 6/1969 | Zirkle | |
| 3,709,879 A | 1/1973 | Amin et al. | |
| 4,705,854 A | 11/1987 | Leighton | |
| 4,711,889 A | 12/1987 | Brombacher et al. | |

FOREIGN PATENT DOCUMENTS

| | | |
|---|---|---|
| GB | 2132194 A | 7/1984 |
| JP | 462509 B | 1/1971 |
| JP | 502513 B | 1/1975 |
| JP | 59110684 A | 6/1984 |
| JP | 60155165 A | 8/1985 |
| JP | 6144884 A | 3/1986 |
| JP | 5163256 A | 6/1993 |

Primary Examiner—Charanjit S. Aulakh
(74) Attorney, Agent, or Firm—Birch, Stewart, Kolasch & Birch, LLP

(57) ABSTRACT

A phenothiazine, acridan, acridone oxime, acridone hydrazone and dibenzodiazepine derivative represented by formula (I)

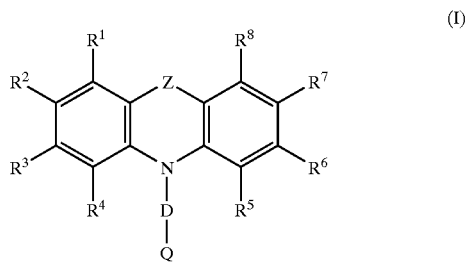

effective against diseases in which histamine, leukotrienes, etc. participate and effective in preventing or treating diseases in which chemical mediators such as histamine and leukotrienes participate, for example, asthma, allergic rhinitis, atopic dermatitis, urticaria, hay fever, gastrointestinal allergy and food allergy.

22 Claims, No Drawings

NITROGEN-CONTAINING TRICYCLIC COMPOUNDS AND DRUGS CONTAINING THE SAME

This application is a divisional of application Ser. No. 09/125,451, filed on Sep. 21, 1998, now U.S. Pat. No. 6,333,322, and for which priority is claimed under 35 U.S.C. § 120. application Ser. No. 09/125,451 is the national phase of PCT International application Ser. No. PCT/JP97/00789 filed on Mar. 13, 1997 under 35 U.S.C. § 371. The entire contents of each of the above-identified applications are hereby incorporated by reference. This application also claims priority of Application No. 8-055628 filed in Japan on Mar. 13, 1996 under 35 U.S.C. § 119.

BACKGROUND OF THE INVENTION

1. Technical Field

The present invention relates to a nitrogen-containing tricyclic compound useful as a medicine, a medicine containing the same and processes for producing the same. More particularly, it relates to a novel nitrogen-containing tricyclic compound useful as a medicine for diseases against which the effect of inhibiting the binding of IgE receptor γ to a tyrosine kinase of 72 kDa is efficacious.

2. Prior Art

The bronchial asthma and the atopic diseases in human beings appear in consequence of highly intriacte vital reactions. It is suspected that most of these conditions are caused because various chemical mediators liberated from mast cells and basophils, as triggered by antigen-antibody reactions, induce vital disturbances as by contracting such smooth muscles as bronchial muscles and vessels of the pulmonary circulation or enhancing permeability of blood vessels.

As the chemical mediators liberated from mast cells and basophils, histamine, leukotrienes, prostaglandins, TNF, etc. have been known. It is well known that histamine, among other substances mentioned above, is the most significant chemical mediator for the allergic rhinitis and the urticaria in human beings. The leucotrienes comprise leucotrienes $B_4$, $C_4$, and $D_4$ and the relation thereof with the asthmatic convulsion has been attracting attention.

Heretofore, the development of medicines for the prevention, alleviation, or elimination of the crisis of symptoms of allergic diseases has been aimed at repressing the creation and liberation of such chemical mediators or antagonizing the effects thereof.

Sodium cromoglycate (Intal™) having been marketed since 1969 is a typical example of these drugs.

However, the conventional antiallergic agents typified by Intal™ show difference in the chemical mediator liberation inhibitory concentration between in vitro and in vivo. Moreover, sensitivities to these drugs widely vary from patient to patient and their action mechanisms still remain unknown in many points.

Mast cells and basophils closely relating to allergic diseases have a highly affinitive receptor, Fcε RI, for the IgE antibody on the cell membrane thereof. IgE antibody's binding to this receptor forms a cross-linkage with the corresponding polyvalent antigen, the intracellular signal transmission mechanism is activated. Then histamine is liberated or leucotrienes and prostaglandins are formed and liberated, thus inducing the onset of the so-called allergic symptoms. It is furthermore considered that the cytokines such as TNF and interleukins thus produced interact with other cells and thus make the diseases chronic.

Under these circumstances, the present inventors have paid their attention to the activation of a non-receptor type tyrosine kinase located at the early stage in the activation of the intracellular signal transmission mechanism upon liberation of chemical mediators from mast cells or basophils. It is known that this tyrosine kinase is activated when it binds to the phosphorylated tyrosine activation motif (TAM) region in the IgE receptor γ chain. By inhibiting this binding to thereby inhibit the activation of the tyrosine kinase of 72 kDa, the activation of the intracellular signal transmission mechanism depending on the IgE antibody in mast cells or basophils can be inhibited. As a result, also the liberation of the above chemical mediators can be inhibited. The present inventors have found out that desired objects can be achieved by using nitrogen-containing tricyclic compounds represented by the following formula (I), thus completing the present invention.

DISCLOSURE OF THE INVENTION

An object of the present invention is to provide a novel acridone derivative and a pharmacologically acceptable salt thereof which is efficacious in preventing or treating asthma, allergic rhinitis, atopic dermatitis, urticaria, hay fever, gastrointestinal allergy, food allergy, etc. Another object of the present invention is to provide a medicine containing as the active ingredient the compound, a hydrate thereof or a pharmacologically acceptable salt thereof.

Accordingly, the present invention relates to a nitrogen-containing tricyclic compound represented by the following formula (I), a hydrate thereof or a pharmacologically acceptable salt thereof:

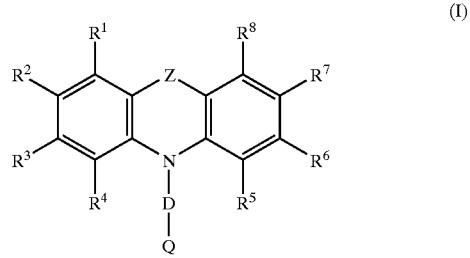

wherein $R^1$, $R^2$, $R^3$, $R^4$, $R^5$, $R^6$, $R^7$ and $R^8$ are the same or different from each other and each represents hydrogen, hydroxy, cyano, nitro, optionally substituted carbamoyl, halogeno, optionally halogenated lower alkyl, optionally substituted cycloalkyl, optionally halogenated lower alkoxy, acyl, optionally protected carboxy, optionally substituted aryl, optionally substituted heteroaryl, cycloalkylalkyl, hydroxylated alkyl, alkoxyalkyl, optionally protected carboxyalkyl, optionally substituted arylalkyl, optionally substituted heteroarylalkyl, cyanoalkyl, acylalkyl, optionally substituted carbamoylalkyl, optionally halogenated alkenyl, hydroxyalkenyl, alkoxyalkenyl, optionally protected carboxyalkenyl, optionally substituted arylalkenyl, optionally substituted heteroarylalkenyl, cyanoalkenyl, acylalkenyl, optionally substituted carbamoylalkenyl, optionally halogenated alkynyl, hydroxyalkynyl, alkoxyalkynyl, optionally protected carboxyalkynyl, optionally substituted arylalkynyl, optionally substituted heteroarylalkynyl, cyanoalkynyl, acylalkynyl, optionally substituted carbamoylalkynyl, hydroxyalkoxy, alkoxyalkoxy, optionally protected carboxyalkoxy, optionally substituted arylalkoxy, optionally substituted heteroarylalkoxy, —A—NR$^9$R$^{10}$ [wherein A represents optionally substituted alkylene, optionally substituted alkenylene, optionally substituted alkynylene or a single bond; and R$^9$ and R$^{10}$ are the same or different from each other and each represents hydrogen, optionally halogenated lower alkyl, optionally substituted aryl or acyl, or R$^9$ and R$^{10}$ may form together with the nitrogen atom to which they are bonded a ring optionally having additional nitrogen, oxygen or sulfur], or

[wherein B represents optionally substituted alkylene, optionally substituted alkenylene, optionally substituted alkynylene or a single bond; R$^{11}$ represents optionally halogenated lower alkyl or amino optionally substituted by lower alkyl; and x represents an integer of from 0 to 2];
provided that two of R$^1$, R$^2$, R$^3$, R$^4$, R$^5$, R$^6$, R$^7$ and R$^8$ adjacent to each other may form together with the carbon atom to which they are bonded a ring optionally containing oxygen, sulfur or nitrogen and optionally substituted;
z represents

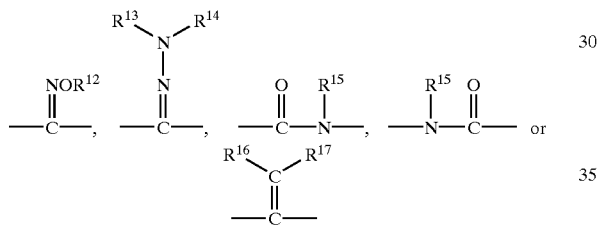

[wherein y represents an integer of from 0 to 2],

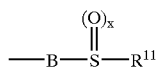

[wherein y represents an integer of from 0 to 2],
[wherein R$^{12}$, R$^{13}$, R$^{14}$, R$^{15}$, R$^{16}$ and R$^{17}$ are the same or different from each other and each represents hydrogen, optionally substituted carbamoyl, optionally halogenated lower alkyl, optionally substituted cycloalkyl, acyl, optionally halogenated lower alkylsulfonyl, optionally substituted arylsulfonyl, optionally protected carboxy, optionally substituted aryl, optionally substituted heteroaryl, cycloalkylalkyl, hydroxylated alkyl, alkoxyalkyl, optionally protected carboxyalkyl, optionally substituted arylalkyl, optionally substituted heteroarylalkyl, cyanoalkyl, acylalkyl, optionally substituted carbamoylalkyl, optionally halogenated alkenyl, hydroxyalkenyl, alkoxyalkenyl, optionally protected carboxyalkenyl, optionally substituted arylalkenyl, optionally substituted heteroarylalkenyl, cyanoalkenyl, acylalkenyl, optionally substituted carbamoylalkenyl, optionally halogenated alkynyl, hydroxyalkynyl, alkoxyalkynyl, optionally protected carboxyalkynyl, optionally substituted arylalkynyl, optionally substituted heteroarylalkynyl, cyanoalkynyl, acylalkynyl, optionally substituted carbamoylalkynyl, —W—NR$^{18}$R$^{19}$ (wherein W represents optionally branched alkylene, optionally branched alkenylene, optionally branched alkynylene or a single bond; R$^{18}$ and R$^{19}$ are the same or different from each other and each represents hydrogen, optionally halogenated lower alkyl or acyl, or R$^{18}$ and R$^{19}$ may form together with the nitrogen atom to which they are bonded a ring optionally containing additional nitrogen, oxygen or sulfur)];
D represents optionally substituted alkylene, optionally substituted alkenylene, optionally substituted alkynylene or

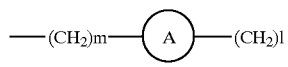

(wherein m and l are each an integer of from 0 to 6; the ring A means an optionally substituted hydrocarbon ring or an optionally substituted heterocycle); and
Q represents optionally substituted carbamoyl, acyl, acylalkyl, optionally protected carboxy, optionally substituted heteroaryl, or —NR$^{20}$R$^{21}$ (wherein R$^{20}$ and R$^{21}$ are the same or different from each other and each represents hydrogen, optionally halogenated lower alkyl, optionally halogenated lower alkoxy, hydroxylated alkyl, alkoxyalkyl, optionally substituted aryl, optionally substituted arylalkyl, optionally substituted heteroaryl, optionally substituted heteroarylalkyl, optionally substituted aryloxy, optionally substituted arylalkoxy, optionally substituted heteroaryloxy, optionally substituted heteroarylalkoxy, optionally protected carboxyalkyl, acyl, optionally substituted acylalkyl, optionally substituted acylamino, optionally substituted acylaminoalkyl, cyanoalkyl, optionally substituted carbamoylalkyl, optionally substituted aminoalkyl, cyanoalkyl, acylalkyl, cycloalkyl, cycloalkylalkyl or amidino optionally substituted by lower alkyl, or R$^{20}$ and R$^{21}$ may form together with the nitrogen atom to which they are bonded an optionally substituted 3- to 8-membered ring which may have, as its ring-member other than carbon, at least one member selected from the group consisting of nitrogen, sulfur, oxygen and —NR$^{22}$ (wherein R$^{22}$ represents hydrogen, optionally halogenated lower alkyl, acyl, optionally substituted acylalkyl, optionally substituted aryl, optionally substituted heteroaryl, optionally substituted arylalkyl, optionally substituted heteroarylalkyl or —S(O)$_s$—(Y)$_u$—R$^{23}$ (wherein R$^{23}$ represents hydrogen, optionally halogenated lower alkyl or optionally substituted aryl; Y represents methylene; s is an integer of from 0 to 2; and u is 0 or 1))];
provided that the following cases are excluded:
(1) the one where R$^5$ and R$^6$ are both hydrogen atoms;
(2) the one where Z is

[wherein y is an integer of from 0 to 2]; R$^5$ is fluoro; and R$^6$ is fluoro or trifluoromethyl; and (3) the one where Z is

[wherein y is an integer of from 0 to 2]; $R^5$ is carboxy; and $R^6$ is chloro}.

DETAILED DESCRIPTION OF THE INVENTION

The term "halogen atom" as used in the definition of $R^1$, $R^2$, $R^3$, $R^4$, $R^5$, $R^6$, $R^7$ and $R^8$ in the formula (I) means fluorine, chlorine, bromine, iodine, etc.

The term "lower alkyl" in "optionally halogenated lower alkyl" as used in the definition of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ means linear or branched $C_{1-6}$ alkyl, for example, methyl, ethyl, n-propyl, isopropyl, n-butyl, isobutyl, sec-butyl, tert-butyl, n-pentyl, 1,2-dimethylpropyl, 1,1-dimethylpropyl, 2,2-dimethylpropyl, 2-ethylpropyl, n-hexyl, 1,2-dimethylbutyl, 2,3-dimethylbutyl, 1,3-dimethylbutyl, 1-ethyl-2-methylpropyl and 1-methyl-2-ethylpropyl groups.

In such a case, the term "optionally halogenated" means that the above alkyl may be substituted by 1 to 3 halogen atoms such as fluorine, chlorine, bromine or iodine. Namely, the "optionally halogenated lower alkyl" as used in the formula (I) includes trifluoromethyl, dibromoethyl and the like.

The term "lower alkenyl" in "optionally halogenated lower alkenyl" as used in the definition of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{20}$ and $R^{21}$ means linear or branched $C_{1-6}$ alkenyl, for example, vinyl, 1-propenyl, 2-propenyl, isopropenyl, 2-methyl-1-propenyl, 3-methyl-1-propenyl, 2-methyl-2-propenyl, 3-methyl-2-propenyl, 1-butenyl, 2-butenyl and 3-butenyl groups. The lower alkenyl as used herein further includes the above-mentioned alkenyl substituted by 1 to 3 halogen atoms.

The term "lower alkynyl" in "optionally halogenated lower alkynyl" as used in the definition of $R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, $R^{20}$ and $R^{21}$ means linear or branched $C_{1-6}$ alkynyl, for example, ethynyl, 1-propynyl, 2-propynyl, 1-butynyl, 2-butynyl, 3-butynyl, 3-methyl-1-propynyl and 2-methyl-3-propynyl groups. The lower alkynyl as used herein further includes the above-mentioned alkynyl substituted by 1 to 3 halogen atoms.

The term "cycloalkyl" in "optionally substituted cycloalkyl" as used in the definition of $R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, $R^{20}$ and $R^{21}$ means $C_{3-8}$ ones such as cyclopropyl, cyclobutyl, cyclopentyl, cyclohexyl, cycloheptyl and cyclooctyl groups.

The term "cycloalkylalkyl" as used in the definition of $R^1$, $R^2$, $R^3$, $R^4$, $R^5$, $R^6$, $R^7$ and $R^8$ means those wherein the above lower alkyl is attached to any carbon atom of the above cycloalkyl.

The term "lower alkoxy" in "optionally halogenated lower alkoxy" as used in the definition of $R^1$, $R^2$, $R^3$, $R^4$, $R^5$, $R^6$, $R^7$, $R^8$, $R^{20}$ and $R^{21}$ means linear or branched $C_{16}$ alkoxy, for example, methoxy, ethoxy, n-propoxy, isopropoxy, n-butoxy, sec-butoxy, tert-butoxy, n-pentyloxy, 1,2-dimethylpropyloxy, 1,1-dimethylpropyloxy, 2,2-dimethylpropyloxy, 2-ethylpropyloxy, n-hexyloxy, 1,2-dimethylbutyloxy, 2, 3-dimethylbutyloxy, 1,3-dimethylbutyloxy, 1-ethyl-2-methylpropyloxy and 1-methyl-2-ethylpropyloxy groups.

In such a case, the term "optionally halogenated" means that the above alkoxy may be substituted by 1 to 3 halogen atoms such as fluorine, chlorine, bromine or iodine. Namely, the "optionally halogenated lower alkoxy" as used herein includes trifluoromethoxy, dibromoethoxy and the like.

The term "acyl" as used in the definition of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and Q means those derived from saturated aliphatic monocarboxylic acids such as acetyl, propionyl, butyryl, valeryl, isovaleryl and pivaloyl groups, those derived from unsaturated aliphatic carboxylic acids such as acryloyl, propioloyl, methacryloyl, crotonoyl and isocrotonoyl groups, those derived from carbocyclic carboxylic acids such as benzoyl, naphthoyl, toluoyl, hydroatropoyl, atropoyl and cinnamoyl groups, those derived from heterocyclic carboxylic acids such as furoyl, thenoyl, nicotinoyl and isonicotinoyl groups, those derived from hydroxy carboxylic acids or alkoxy carboxylic acids such as glycoloyl, lactoyl, glyceroyl, tropoyl, benzyloyl, salicyloyl, anisoyl, vaniloyl, piperonyloyl and galloyl groups and those derived from various amino acids.

The term "acylalkyl" as used in the definition of $R^1$, $R^2$, $R^3$, $R^4$, $R^5$, $R^6$, $R^7$, $R^8$, $R^9$, $R^{10}$, $R^{12}$, $R^{12}$, $R^{13}$, $R^{14}$, $R^{15}$, $R^{16}$, $R^{17}$, $R^{20}$, $R^{21}$, $R^{22}$ and Q means those wherein the above acyl is attached to any carbon atom of the above lower alkyl. Examples thereof include acetylmethyl, propionylmethyl, benzoylethyl, naphthoylpropyl, cinnamoylpropyl, salicyloylbutyl, nicotinoylpentyl and glyceroylhexyl groups, though, needless to say, the present invention is not restricted thereto.

The term "acylalkenyl" as used in the definition of $R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$ and $R^{17}$ means those wherein the acyl is attached to any carbon atom of the above alkenyl. Examples thereof include benzoyl-1-ethylenyl and 3-nicotinoyl-2-propylenyl, though, needless to say, the present invention is not restricted thereto.

The term "acylalkynyl" as used in the definition of $R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$ and $R^{17}$ means those wherein the acyl is attached to any carbon atom of the above lower alkynyl.

The term "hydroxylated alkyl" as used in the definition of $R^1$, $R^2$, $R^3$, $R^4$, $R^5$, $R^6$, $R^7$, $R^8$, $R^{12}$, $R^{13}$, $R^{14}$, $R^{15}$, $R^{16}$, $R_{17}$, $R^{20}$ and $R^{21}$ means those wherein 1 to 3 hydroxyl groups are attached to any carbon atom of the above lower alkyl, for example, hydroxymethyl, 1-hydroxyethyl, 2-hydroxyethyl, 1-hydroxypropyl, 2-hydroxypropyl, 3-hydroxypropyl, 2,3-dihydroxypropyl and 3,4-dihydroxybutyl groups.

The term "hydroxyalkenyl" as used in the definition of $R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$ and $R^{17}$ means those wherein hydroxy is attached to any carbon atom of the above lower alkenyl.

The term "hydroxyalkynyl" as used in the definition of $R^1$, $R^2$, $R^3$, $R^4$, $R^5$, $R^6$, $R^7$, $R^8$, $R^9$, $R^{10}$, $R^{12}$, $^{13}$, $R^{14}$, $R^{15}$, $R^{16}$ and $R^{17}$ means those wherein hydroxy is attached to any carbon atom of the above lower alkynyl.

The term "alkoxyalkyl" as used in the definition of $R^1$, $R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, $R^{20}$ and $R^{21}$ means those wherein the above lower alkoxy is attached to any carbon atom of the above lower alkyl, for example, methoxymethyl, ethoxymethyl, ethoxyethyl and 2-ethoxypropyl groups, though the present invention is not restricted thereto.

The term "alkoxyalkenyl" as used in the definition of $R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$ and $R^{17}$ means those wherein the above lower alkoxy is attached to any carbon atom of the above lower alkenyl, for example, methoxyethylenyl and ethoxypropylenyl groups, though the present invention is not restricted thereto.

The term "alkoxyalkynyl" as used in the definition of $R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$ and $R^{17}$ means those wherein the above lower alkoxy is attached to any carbon atom of the above lower alkynyl.

The term "cyanoalkyl" as used in the definition of $R^1$, $R^2$, $R^3$, $R^4$, $R^5$, $R^6$, $R^7$, $R^8$, $R^{12}$, $R^{13}$, $R^{14}$, $R^{15}$, $R^{16}$, $R^{17}$, $R^{20}$, $R^{21}$, $R^{22}$ and $R^{23}$ means those wherein cyano is attached to any carbon atom of the above lower alkyl, for example, cyanomethyl, 1-cyanoethyl, 2-cyanoethyl, 1-cyanopropyl and 2-cyanopropyl groups.

The term "cyanoalkenyl" as used in the definition of $R^1$, $R^2$, $R^3$, $R^4$, $R^5$, $R^6$, $R^7$, $R^8$, $R^{12}$, $R^{13}$, $R^{14}$, $R^{15}$, $R^{16}$ and $R^{17}$ means those wherein cyano is attached to any carbon atom of the above lower alkenyl.

The term "cyanoalkynyl" as used in the definition of $R^1$, $R^2$, $R^3$, $R^4$, $R^5$, $R^6$, $R^7$, $R^8$, $R^{12}$, $R^{13}$, $R^{14}$, $R^{15}$, $R^{16}$ and $R^{17}$ means those wherein cyano is attached to any carbon atom of the above lower alkynyl.

The term "hydroxyalkoxy" as used in the definition of $R^1$, $R^2$, $R^3$, $R^4$, $R^5$, $R^6$, $R^7$ and $R^8$ means those wherein hydroxy is attached to any carbon atom of the above lower alkoxy, for example, hydroxymethoxy, 1-hydroxyethoxy, 2-hydroxyethoxy, 1-hydroxypropoxy, 2-hydoxypropoxy and 3-hydroxypropoxy groups.

The term "alkoxyalkoxy" as used in the definition of $R^1$, $R^2$, $R^3$, $R^4$, $R^5$, $R^6$, $R^7$ and $R^8$ means those wherein the above lower alkoxy is attached to any carbon atom of the above lower alkoxy, for example, methoxymethoxy, 1-methoxyethoxy, 2-methoxyethoxy, ethoxymethoxy, 1-ethoxyethoxy, 2-ethoxyethoxy, 1-methoxypropoxy and 2-methoxypropoxy groups.

The term "aryl" in "optionally substituted aryl" as used in the definition of $R^1$, $R^2$, $R^3$, $R^4$, $R^5$, $R^6$, $R^7$, $R^8$, $R^9$, $R^{10}$, $R^{12}$, $R^{13}$, $R^{14}$, $R^{15}$, $R^{16}$, $R^{17}$, $R^{20}$, $R^{21}$, $R^{22}$ and $R^{23}$ means, for example, phenyl, 1-naphthyl, 2-naphthyl and anthracenyl groups.

The term "aryl" in "optionally substituted arylalkyl" as used in the definition of $R^1$, $R^2$, $R^3$, $R^4$, $R^5$, $R^6$, $R^7$, $R^8$, $R^{12}$, $R^{13}$, $R^{14}$, $R^{15}$, $R^{16}$, $R^{17}$, $R^{20}$, $R^{21}$ and $R^{22}$ has the same meaning as the one defined above. In such a case, the term "alkyl" has the same meaning as that of "lower alkyl" defined above.

The term "optionally substituted heteroaryl" as used in the definition of $R^1$, $R^2$, $R^3$, $R^4$, $R^5$, $R^6$, $R^7$, $R^8$, $R^{12}$, $R^{13}$, $R^{14}$, $R^{15}$, $R^{16}$, $R^{17}$, $R^{20}$, $R^{21}$, $R^{22}$ and Q means those derived from single or fused rings containing 1 to 4 heteroatoms of at least one type selected from the group consisting of sulfur, oxygen and nitrogen atoms. Examples thereof include pyrrolyl, thienyl, furyl, thiazolyl, oxazolyl, isothiazolyl, isoxazolyl, imidazolyl, pyrazolyl, thiadiazolyl, oxadiazolyl, triazolyl, tetrazolyl, pyridyl, pyridazinyl, pyrimidinyl, pyrazinyl, indolyl, isoindolyl, benzothienyl, benzofuranyl, isobenzofuranyl, benzimidazolyl, indazolyl, benzotriazolyl, benzothiazolyl, benzoxazolyl, quinolyl, isoquinolyl, cinnolinyl, phthalazyl, quinoxalyl, naphthyridyl, quinazolyl and imidazopyridyl groups.

The term "optionally substituted heteroarylalkyl" as used in the definition of $R^1$, $R^2$, $R^3$, $R^4$, $R^5$, $R^6$, $R^7$, $R^8$, $R^{12}$, $R^{13}$, $R^{14}$, $R^{15}$, $R^{16}$, $R^{17}$, $R^{20}$, $R^{21}$ and $R^{22}$ means those wherein the above heteroaryl is attached to any carbon atom of the above lower alkyl.

The term "optionally substituted heteroarylalkenyl" as used in the definition of $R^1$, $R^2$, $R^3$, $R^4$, $R^5$, $R^6$, $R^7$, $R^8$, $R^{12}$, $R^{13}$, $R^{14}$, $R^{15}$, $R^{16}$ and $R^{17}$ means those wherein the above heteroaryl is attached to any carbon atom of the above lower alkenyl.

The term "optionally substituted heteroarylalkynyl" as used in the definition of $R^1$, $R^2$, $R^3$, $R^4$, $R^5$, $R^6$, $R^7$, $R^8$, $R^{12}$, $R^{13}$, $R^{14}$, $R^{15}$, $R^{16}$ and $R^{17}$ means those wherein the above heteroaryl is attached to any carbon atom of the above lower alkynyl.

The term "optionally substituted carbamoyl" as used in the definition of $R^1$, $R^2$, $R^3$, $R^4$, $R^5$, $R^6$, $R^7$, $R^8$, $R^{12}$, $R^{13}$, $R^{14}$, $R^{15}$, $R^{16}$, $R^{17}$ and Q means carbamoyl optionally having 1 or 2 substituents on the nitrogen atom.

The terms "optionally substituted carbamoylalkyl, carbamoylalkenyl and carbamoylalkynyl" as used in the definition of $R^1$, $R^2$, $R^3$, $R^4$, $R^5$, $R^6$, $R^7$, $R^8$, $R^{12}$, $R^{13}$, $R^{14}$, $R^{15}$, $R^{16}$, $R^{17}$, $R^{20}$ and $R^{21}$ mean those wherein optionally substituted carbamoyl is attached to any carbon atom of the above lower alkyl, alkenyl and alkynyl.

Examples of the substituents in the optionally substituted cycloalkyl, optionally substituted aryl, optionally substituted heteroaryl, optionally substituted arylalkyl, optionally substituted heteroarylalkyl, optionally substituted arylalkenyl, optionally substituted heteroarylalkenyl, optionally substituted arylalkynyl, optionally substituted heteroarylalkynyl, optionally substituted arylalkoxy, optionally substituted heteroarylalkoxy, optionally substituted carbamoyl, optionally substituted carbamoylalkyl, optionally substituted carbamoylalkenyl and optionally substituted carbamoylalkynyl include hydroxy; lower alkyl such as methyl, ethyl, n-propyl and isopropyl; lower alkoxy such as methoxy, ethoxy, n-propoxy and isopropoxy; halogen atom such as fluorine, chlorine, bromine and iodine; cyano; acyl such as acetyl, propionyl and benzoyl; amino; nitro: optionally protected carboxyl; carbamoyl; acylamino; sulfamoyl; alkylsulfonylamino; arylsulfonylamino; heteroaryl; carboxyalkyl; carboxyalkoxy; heteroarylalkyl; heteroarylalkoxy; methylenedioxy; and ethylenedioxy. The substituents are selected therefrom.

Examples of the protective groups in the "optionally protected carboxy" as used in the definition of $R^1$, $R^2$, $R^3$, $R^4$, $R^5$, $R^6$, $R^7$, $R^8$, $R^{12}$, $R^{13}$, $R^{14}$, $R^{15}$, $R^{16}$, $R^{17}$, $R^{20}$, $R^{21}$ and Q include lower alkyl such as methyl, ethyl and tert-butyl; lower alkyl substituted by optionally substituted phenyl such as p-methoxybenzyl, p-nitrobenyl, 3,4-dimethoxybenzyl, diphenylmethyl, trityl and phenethyl; halogenated lower alkyl such as 2,2,2-trichloroethyl and 2-iodoethyl; lower alkanoyloxy-substituted lower alkyl such as pivaloyloxymethyl, acetoxymethyl, propionyloxymethyl, butyryloxymethyl, varelyloxymethyl, 1-acetoxyethyl, 2-acetoxyethyl, 1-pivaloyloxyethyl and 2-pivaloyloxyethyl; higher alkanoyloxy-substituted lower alkyl such as palmitoyloxyethyl, heptadecanoyloxymethyl and 1-palmitoyloxyethyl; lower alkoxycarbonyloxy-substituted lower alkyl such as methoxycarbonyloxymethyl, 1-butoxycarbonyloxyethyl and 1-(isopropoxycarbonyloxy) ethyl; carboxy-substituted lower alkyl such as carboxymethyl and 2-carboxyethyl; benzoyloxy-substituted lower alkyl optionally substituted by heteroaryl such as 3-phthalidyl, 4-glycyloxybenzoyloxymethyl, etc.;

(substituted dioxolene)-substituted lower alkyl such as (5-methyl-2-oxo-1,3-dioxolen-4-yl)methyl; cycloalkyl-substituted lower alkanoyloxy-substituted lower alkyl such as 1-cyclohexylacetyloxyethyl; and cycloalkyloxycarbonyloxy-substituted lower alkyl such as 1-cyclohexyloxycarbonyloxyethyl. Moreover, various acid amides are also usable therefor. In summary, the carboxy-protective group may be an arbitrary one, so long as it is decomposed by some means to give a carboxylic acid in vivo.

The term "optionally protected carboxylalkyl" as used in the definition of $R^1$, $R^2$, $R^3$, $R^4$, $R^5$, $R^6$, $R^7$, $R^8$, $R^{12}$, $R^{13}$, $R^{14}$, $R^{15}$, $R^{16}$, $R^{17}$, $R^{20}$ and $R^{21}$ means those wherein carboxy optionally having the above protective group(s) is attached to any carbon atom of the above lower alkyl.

The term "optionally protected carboxylalkoxy" as used in the definition of $R^1$, $R^2$, $R^3$, $R^4$, $R^5$, $R^6$, $R^7$, $R^8$, $R^{12}$, $R^{13}$, $R^{14}$, $R^{15}$, $R^{16}$, $R^{17}$, $R^{20}$ and $R^{21}$ means those wherein optionally protected carboxy is attached to any carbon atom of the above lower alkoxy. In such a case, the protective group has the same meaning as the one defined above.

The term "optionally protected carboxyalkenyl" as used in the definition of $R^1$, $R^2$, $R^3$, $R^4$, $R^5$, $R^6$, $R^7$, $R^8$, $R^{12}$, $R^{13}$, $R^{14}$, $R^{15}$, $R^{16}$ and $R^{17}$ means those wherein optionally protected carboxy is attached to any carbon atom of the above lower alkenyl. In such a case, the protective group has the same meaning as the one defined above.

The term "optionally protected carboxyalkynyl" as used in the definition of $R^1$, $R^2$, $R^3$, $R^4$, $R^5$, $R^6$, $R^7$, $R^8$, $R^{12}$, $R^{13}$, $R^{14}$, $R^{15}$, $R^{16}$ and $R^{17}$ means those wherein optionally protected carboxy is attached to any carbon atom of the above lower alkynyl. In such a case, the protective group has the same meaning as the one defined above.

Examples of the ring in "$R^{20}$ and $R^{21}$ may form together with the nitrogen atom to which they are bonded a ring" of the formula —$NR^{20}R^{21}$ as used in the definition of Q include aziridine, azetidine, pyrrolidine, piperidine, perhydroazepine, perhydroazocine, piperazine, homopiperazine, morpholine, thiomorpholine, thiomorpholine dioxide, indoline, isoindoline, 1,2,3,4-tetrahydroquinoline, 1,2,3,4-tetrahydroisoquinoline, 2,3-dihdyrobenzoxazine, 2,3-dihydrobenzothiazine, pyrrole, imidazole, pyrazole, triazole, tetrazole, indole, isoindole, indazole and benzotriazole.

(a) The term "alkylene" as used in the definition of A, B and W means methylene, ethylene, trimethylene, tetramethylene, pentamethylene or hexamethylene.
(b) The term "alkenylene" as used in the definition of A, B and W means ethenylene, propenylene, butenylene, pentenylene, hexenylene, butanedienylene, pentanedienylene, hexanedienylene or hexanetrienylene.
(c) The term "alkynylene" as used in the definition of A, B and W means ethynylene, propynylene, butynylene, pentynylene, hexynylene, butanediynylene, pentanediynylene, hexanediynylene or hexanetriynylene.
(d) The term "hydrocarbon ring" as used in the definition of the ring A means cyclopropane, cyclobutane, cyclopentane, cyclohexane, benzene, naphthalene, etc.
(e) The term "heterocycle" as used in the definition of the ring A means pyrrolidine, piperidine, piperazine, morpholine, thiomorpholine, homopiperazine, pyrrole, pyrazole, imidazole, triazole, tetrazole, oxazole, thiazole, thiadiazole, pyridine, pyridazine, pyrimidine, pyrazine, indole, imidazopyridine, quinoline, naphthyridine, phthalazine, etc.

In the case of the compounds of the present invention having asymmetric carbon atoms, it is needless to say that the optical isomers thereof are also included in the scope of the present invention. Furthermore, hydrates thereof are included in the scope of the present invention.

Examples of the pharmacologically acceptable salts as used in the present invention include inorganic acid salts such as hydrochlorides, hydrobromides, sulfates and phosphates; organic acid salts such as acetates, maleates, tartrates, methanesulfonates, benzenesulfonates and toluenesulfonates; and salts of amino acids such as aspartic and glutamic acids.

To facilitate the understanding of the present invention, and not by way of limitation, typical examples of the compounds of the present invention will be given. Each compound is expressed in a free state:

1) 1,2-dimethyl-10-[3-[(2-hydroxy-3-methylphenyl) methylamino]propyl]phenothiazine-5-dioxide
2) 1,2-dimethyl-10-[3-[(3-chloro-2-hydroxyphenyl) methylamino]propyl]phenothiazine-5-dioxide
3) 1,2-dimethyl-10-[3-[(5-methoxy-2-furanyl)methylamino] propyl]phenothiazine-5-dioxide
4) 1,2-dimethyl-10-[3-[(3-methoxy-2-thienyl)methylamino] propyl]phenothiazine-5-dioxide
5) 1,2-dimethyl-10-[3-(4-hydroxy-4-phenylpiperidinyl) propyl]phenothiazine-5-dioxide
6) 1,2-dimethyl-10-[3-(4-benzylpiperazinyl)propyl] phenothiazine-5-dioxide
7) 1,2-dimethyl-10-[3-[N-[(2-hydroxyphenyl)methyl] methylamino]propyl]-phenothiazine-5-dioxide
8) 1,2-dimethyl-10-[3-[N-[(2-hydroxy-3-methylphenyl) methyl]methylamino]propyl]-phenothiazine-5-dioxide
9) (E,Z)-3,4-dimethyl-10-(3-benzylaminopropyl)-9-acridoneoxime-O-(2-carboxyethyl) ether.
10) (E,Z)-3,4-dimethyl-10-(3-benzylaminopropyl)-9-acridoneoxime-O-(1-carboxyethyl) ether.

MODE FOR CARRYING OUT THE INVENTION

The compounds of the present invention can be produced by combining generally known methods. Now, main processes generally usable for producing the compounds of the present invention will be illustrated.

Production Process 1

Compounds of the formula (I) wherein Z is —$S(O)_y$— and Q is —$NR^{20}R^{21}$ can be produced by the following process.

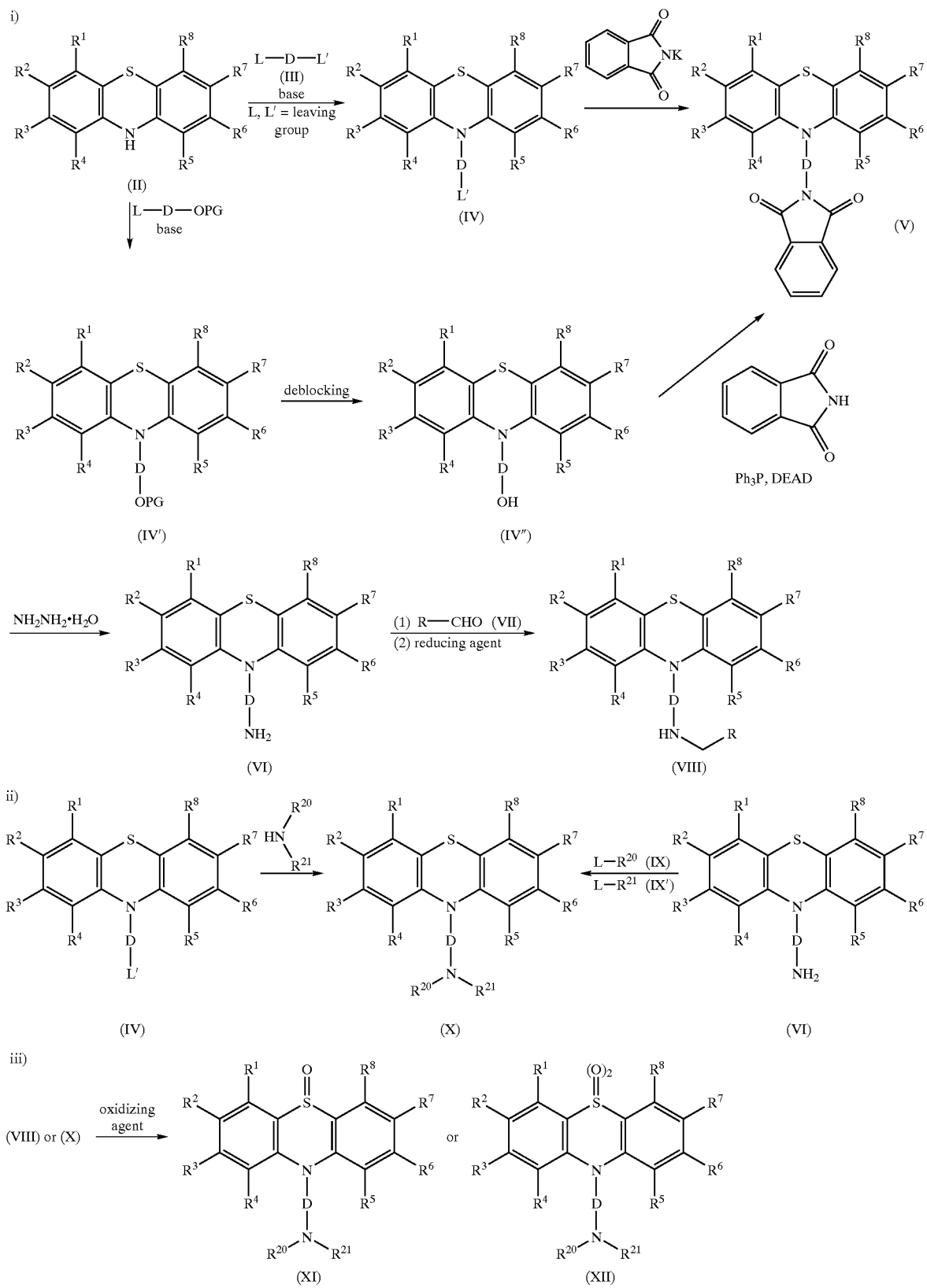

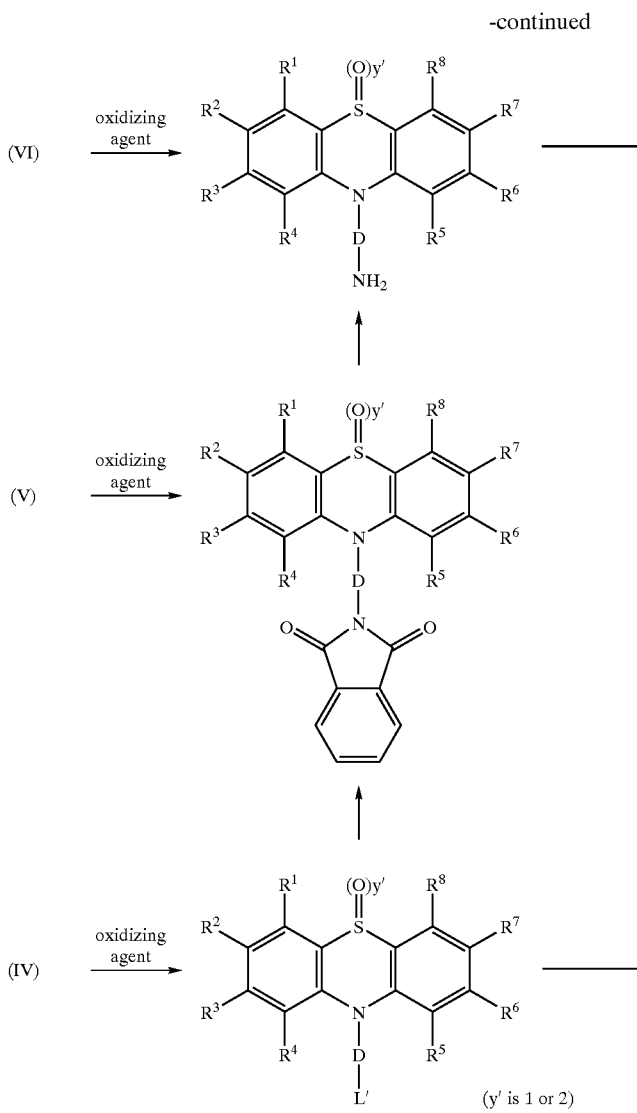

i) A phenothiazine derivative represented by the formula (II) synthesized by a publicly known method [for example, those described in J. Org. Chem., 20, 1577 (1955).; ibid., 35, 4254 (1970).; J. Chem. Soc., (C) 2437 (1970).; and Chem. Ind., 238 (1966).] is reacted in the presence of a base with a compound represented by the formula (III) having leaving groups at both ends to thereby give a phenothiazine derivative represented by the formula (IV). Preferable examples of the base usable herein include sodium hydride, n-butyllithium and t-butoxypotassium. Preferable examples of the leaving groups include halogeno and sulfonate. Any reaction solvent may be used therefor, so long as it remains inert during the reaction. Next, the leaving group L' in the compound (IV) is substituted by phthalimide. The resulting phthalimide compound represented by the formula (V) is then treated with hydrazine hydrate to give an amine compound represented by the general formula (VI). Next, this amine compound (VI) is condensed under dehydration with an aldehyde compound (VII: wherein R represents alkyl, alkenyl, alkynyl, aryl or heteroaryl). The Schiff base thus obtained is then treated with a reducing agent such as sodium borohydride to give analkylamine compound represented by the formula (VIII). Any reaction solvent may be used therefor, so long as it remains inert during the reaction.

Alternatively, the phthalimide compound (V) serving as an intermediate may be synthesized in the following manner. Namely, the compound (II) is reacted with a compound having a leaving group L at one end and a protected hydroxyl group at another end to give a compound represented by the formula (IV'). Subsequently, the compound (IV') is deblocked in a conventional manner to give an alcohol (IV"), which is then reacted with phthalimide under the conditions of the Mitsunobu reaction to give a phthalimide compound.

ii) The compound (IV) is treated with a primary or secondary amine, or the compound (VI) is treated with a compound having a leaving group L (IX and/or X') to give a compound represented by the formula (X).

iii) A sulfoxide compound (XI) and a sulfonyl compound (XII) can be produced by oxidizing the sulfur atoms in the compounds (VIII) and (IX) or oxidizing the sulfur atom in the stage of the intermediate (IV) or (VI) in the process of the above i) or ii) followed by appropriate reactions.

Production Process 2

Compounds of the formula (I) wherein Z is —C(=NOR$^{12}$)— or —C(=NNR$^{13}$R$^{14}$) and Q is —NR$^{20}$R$^{21}$ can be produced by the following process.

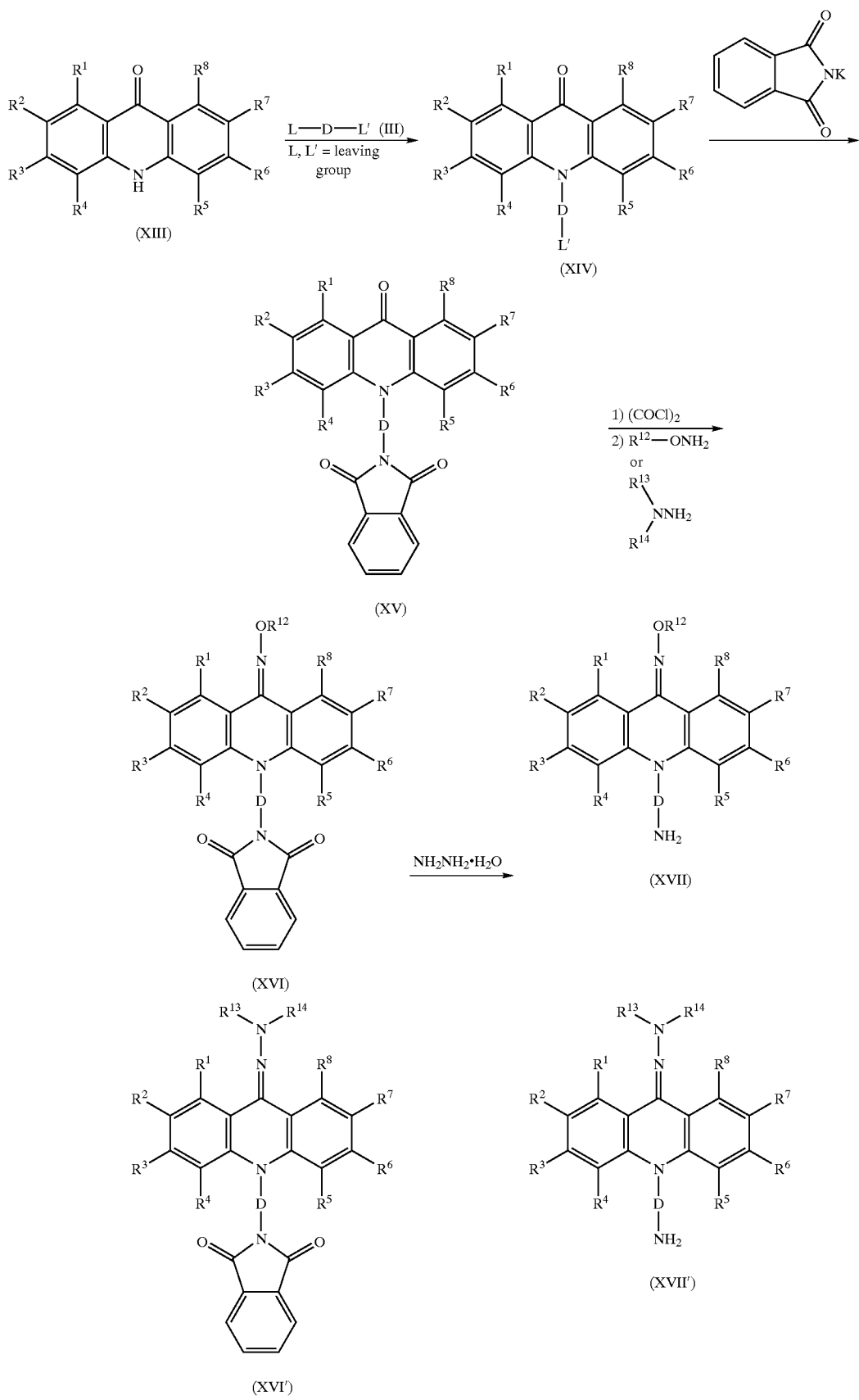

An acridone compound (XIII) synthesized by a publicly known method (for example, the one described in JP-A 7-3161359) is reacted with a compound (III) to give a compound (XIV). Next, this compound (XIV) is reacted with potassium phthalimide to give a compound (XV). Then the compound (XV) is reacted with oxalyl chloride. The acridinium salt thus obtained is reacted with a hydroxylamine derivative ($R^{12}ONH_2$: wherein $R^{12}$ is as defined above) or a hydrazine derivative ($R^{13}R^{14}NNH_2$: wherein $R^{13}$ and $R^{14}$ are each as defined above) to give a compound represented by the formula (XVI) or (XVI'). Then the obtained compound is reacted with hydrazine hydrate to give a primary amine compound represented by the formula (XVII) or (XVII'). Further, secondary or tertiary amines can be produced in accordance with the methods of i) of ii) in the above production process 1.

Production Process 3

Compounds represented by the formula (I) wherein Z is —C(=CR$^{16}$R$^{17}$)— and Q is —NR$^{20}$R$^{21}$ can be produced by the following process.

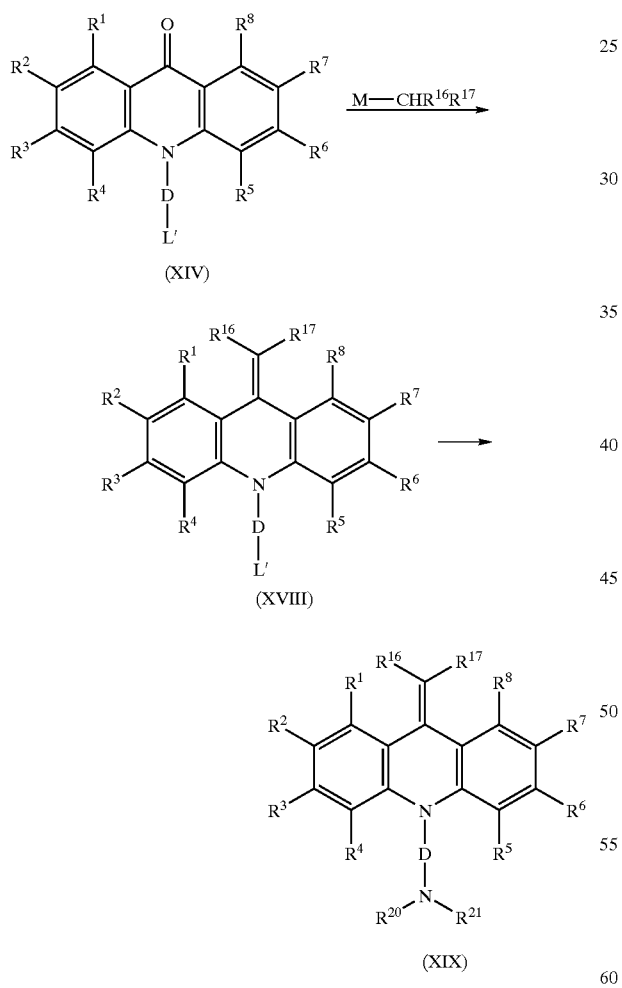

The compound represented by the formula (XIV) given in the production process 2 is reacted with a metal compound M—CHR$^{16}$R$^{17}$ (wherein M means a metal and R$^{16}$ and R$^{17}$ are each as defined above such as alkyl lithium, etc.) to give an acridan compound represented by the formula (XVIII). Next, this product is treated in the same manner as the one described in the production process 1 ii) to give an amine compound represented by the formula (IX).

Production Process 4

Compounds represented by the formula (I) wherein Z is —C(=O)N(R$^{15}$)— or —N(R$^{15}$C(=O)—and Q is —NR$^{20}$R$^{21}$ can be produced by the following process.

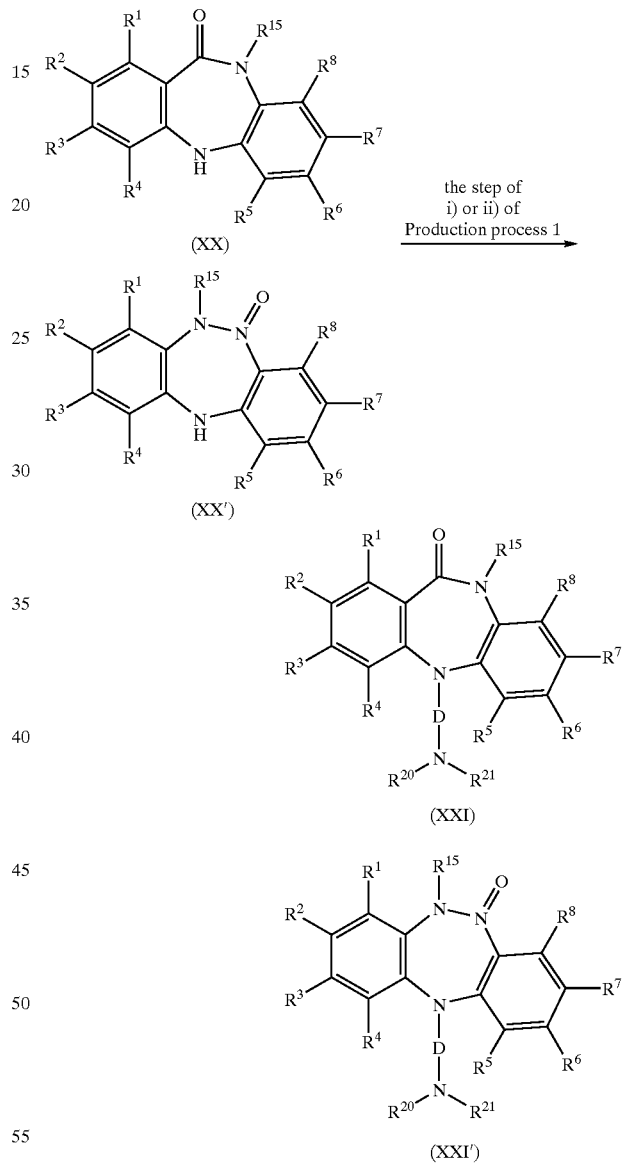

The procedure of the step i) or ii) in the production process 1 was repeated while replacing the phenothiazine derivative represented by the formula (II) employed in the production process 1 by a dibenzodiazepine derivative (XX or XX') produced by a publicly known method [Indian J. Chem., 23B, 85 (1984).] or Production Example 13 or 14. Thus a compound represented by the formula (XXI or XXI') can be obtained.

Production Process 5

Compounds of the formula (I) wherein Q is heteroaryl can be produced by the following process.

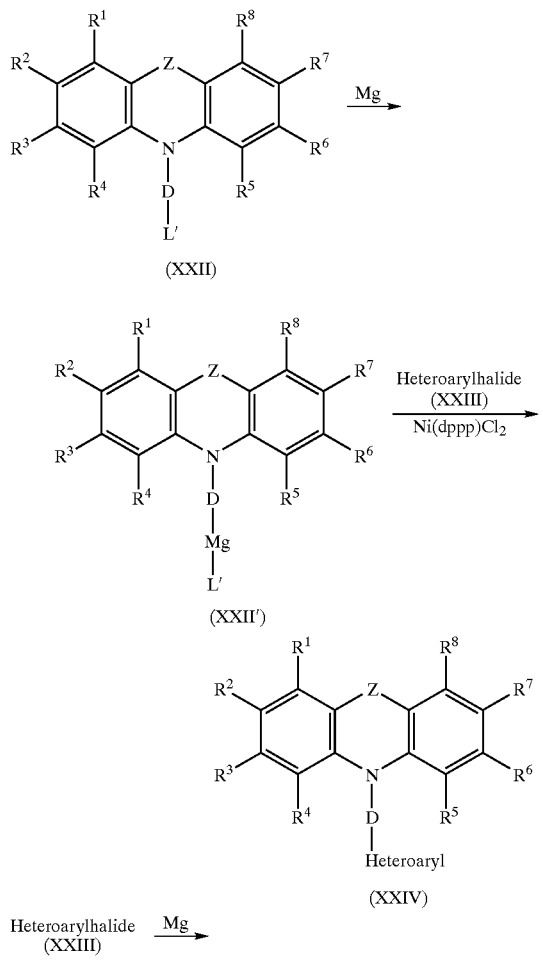

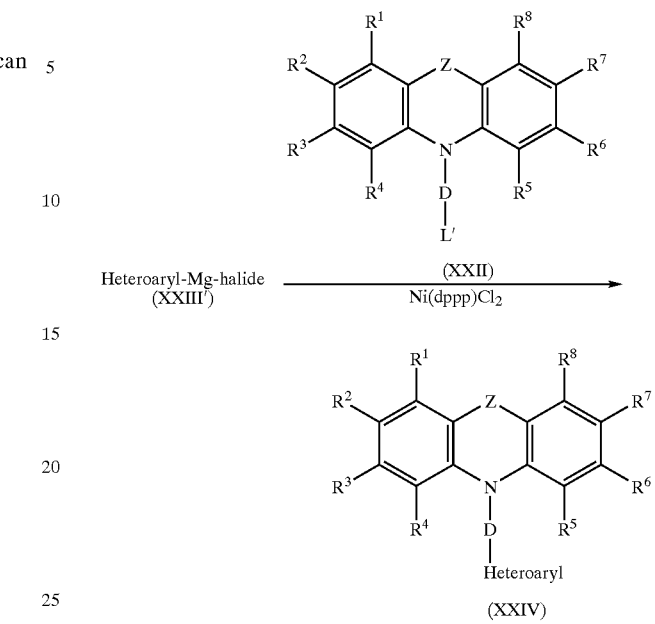

The compound represented by the formula (XXII) obtained by the production processes 1, 2, 3 and 4 and having a leaving group L' is treated with magnesium to give a Grignard reagent. Next, this Grignard reagent is reacted with an optionally substituted heteroaryl halide derived from, e.g., pyridine or pyrimidine in the presence of 1,3-bis (diphenylphosphino)propane nickel dichloride [Ni(dppp) Cl$_2$] to give a compound represented by the formula (XXIV).

Production Process 6

Compounds of the formula (I) wherein Q is optionally substituted carbamoyl, acyl or optionally protected carboxy can be produced by the following process.

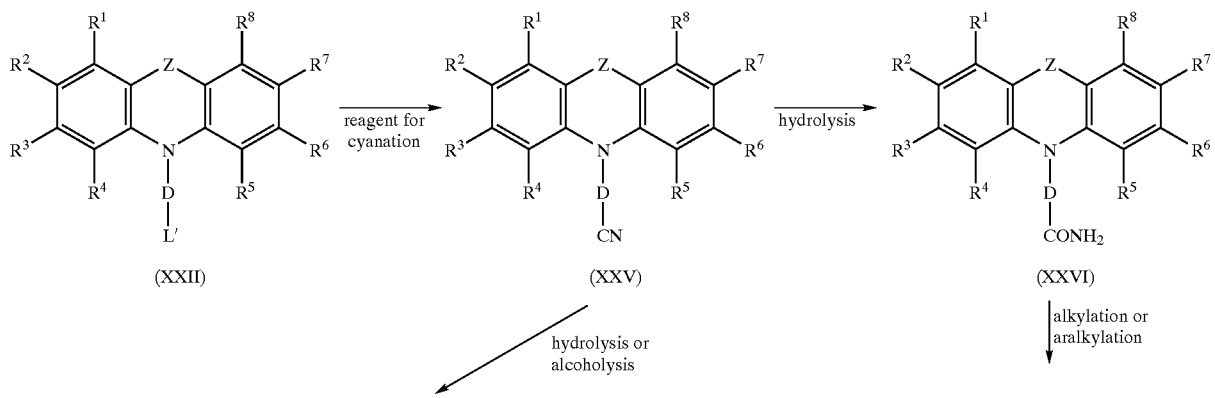

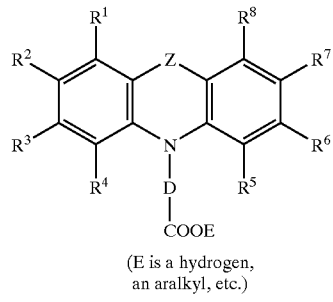

(E is a hydrogen,
an aralkyl, etc.)

(XXVII)

primary or
secondary amine
⎯⎯⎯⎯⎯⎯⎯⎯⎯⎯→
When E is a hydrogen,
after converting into
a reactive derivative
of an acid.)

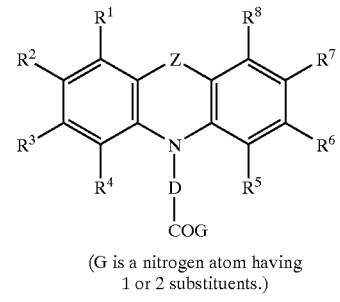

(G is a nitrogen atom having
1 or 2 substituents.)

(XXVIII)

The compound represented by the formula (XXII) obtained by the production processes 1, 2, 3 and 4 and having a leaving group L' is treated with a reagent for cyanation such as sodium cyanide in the presence of a base to give a nitrile compound (XXV), which is then hydrolyzed to give an unsubstituted carbamoyl compound (XXVI) or an ester or carboxylic acid represented by the formula (XXVII). A substituted carbamoyl compound (XXVIII) can be obtained by alkylating or aralkylating the unsubstituted carbamoyl compound (XXVI) or reacting the ester or a reactive derivative (acid halide, reactive ester, etc.) derived from the carboxylic acid in a conventional manner with a primary or a secondary amine. A protected carboxyl compound can be obtained by reacting the reactive derivative derived from the carboxylic acid with an alcohol derivative.

To illustrate the usefulness of the present invention, pharmacological experimental examples will be given.

Pharmacological experimental examples:

(1) Inhibitory Effects on Various Mediators Release from Rat Basophilic Leukemia Cell Line (RBL-2H3)

i) Experimental Method

IgE-sensitized RBL-2H3 cells (i.e., a cell line originating in rat cells) release and produce not only histamine and serotonin but also cytokines such as TNF α and prostaglandins which are inflammatory mediators after stimulation with IgE sepecific antibody. In this experimental system, inhibitory effects on various mediators release were examined by using serotonin as an indication.

The cells were beforehand labeled with [$^3$H]-labeled serotonin and, at the same time, sensitized with the IgE antibody. After incubating with the compounds of the present invention, the cells were stimulated with the specific antigen. Then the inhibitory activity of each compound was calculated from the amount of the [$^3$H]-labeled serotonin thus liberated into the medium and the amount of [$^3$H]-labeled serotonin liberated when no compound of the present invention was added.

ii) Results of the Experiment

The results are shown in Tables 1 to 3.

TABLE 1

Inhibitory effects on various mediators release from rat basophilic leukemia cell line (RBL-2H3)

| Ex.no. | IC$_{50}$ (μM) in serotonin liberation from RBL-2H3 cells | Ex.no. | IC$_{50}$ (μM) in serotonin liberation from RBL-2H3 cells |
|---|---|---|---|
| 1 | 5 | 52 | 3 |
| 3 | 10 | 53 | 0.8 |

TABLE 1-continued

Inhibitory effects on various mediators release from rat basophilic leukemia cell line (RBL-2H3)

| Ex.no. | IC$_{50}$ (μM) in serotonin liberation from RBL-2H3 cells | Ex.no. | IC$_{50}$ (μM) in serotonin liberation from RBL-2H3 cells |
|---|---|---|---|
| 6 | 10 | 54 | 1 |
| 7 | 8 | 55 | 8 |
| 8 | 0.1 | 56 | 3 |
| 9 | 1> | 57 | 2 |
| 10 | 3 | 58 | 2 |
| 22 | 0.1 | 59 | 3 |
| 23 | 2 | 60 | 6 |
| 24 | 3 | 61 | 6 |
| 25 | 3 | 62 | 3 |
| 26 | 2 | 63 | 3 |
| 27 | 3 | 64 | 3 |
| 28 | 0.8 | 65 | 0.5 |
| 29 | 0.8 | 66 | 0.5 |
| 30 | 2 | 67 | 1 |
| 31 | 0.5 | 68 | 4 |
| 32 | 0.5 | 69 | 1 |
| 33 | 1 | 70 | 2 |
| 34 | 2 | 71 | 8 |
| 35 | 1 | 72 | 8 |
| 36 | 1 | 73 | 2 |
| 37 | 2 | 74 | 2 |
| 38 | 8 | 75 | 6 |
| 39 | 2 | 76 | 3 |
| 40 | 5 | 5 | 5 |
| 41 | 5 | 78 | 4 |
| 42 | 2 | 79 | 2 |
| 43 | 4 | 80 | 1 |
| 44 | 1 | 81 | 1 |
| 45 | 1 | 82 | 2 |
| 46 | 0.5 | 83 | 2 |
| 47 | 0.5 | 84 | 2 |
| 48 | 0.3 | 85 | 3 |
| 49 | 2 | 86 | 1 |
| 50 | 2 | 87 | 3 |
| 51 | 2 | 88 | 1 |

TABLE 2

| Ex.no. | IC$_{50}$ (μM) in serotonin liberation from RBL-2H3 cells | Ex.no | IC$_{50}$ (μM) in serotonin liberation from RBL-2H3 cells |
|---|---|---|---|
| 89 | 2 | 129 | <1 |
| 90 | 3 | 130 | 3 |
| 91 | 5 | 131 | 3 |
| 93 | 3 | 132 | 2 |
| 94 | <1 | 133 | 1 |

TABLE 2-continued

| Ex.no. | IC$_{50}$ ($\mu$M) in serotonin liberation from RBL-2H3 cells | Ex.no | IC$_{50}$ ($\mu$M) in serotonin liberation from RBL-2H3 cells |
|---|---|---|---|
| 95 | 3 | 134 | 3 |
| 98 | 0.5 | 135 | 2 |
| 99 | 5 | 136 | 0.8 |
| 100 | 2 | 137 | 1 |
| 101 | 5 | 138 | 3 |
| 102 | 1 | 139 | 2 |
| 103 | <3 | 140 | 3 |
| 104 | <3 | 141 | 0.5 |
| 105 | 2 | 143 | 3 |
| 106 | 2 | 144 | 8 |
| 107 | 2 | 145 | 6 |
| 108 | 2 | 146 | 3 |
| 109 | 3 | 147 | 3 |
| 110 | 1 | 148 | 8 |
| 111 | 2 | 149 | 8 |
| 112 | 1 | 150 | 1 |
| 113 | 3 | 151 | 2 |
| 114 | 2 | 152 | 1 |
| 115 | 3 | 153 | 6 |
| 116 | 10 | 154 | 6 |
| 117 | 2 | 155 | 4 |
| 118 | 10 | 156 | 3 |
| 119 | 6 | 157 | 1 |
| 120 | 3 | 158 | 3 |
| 121 | 1 | 159 | 5 |
| 122 | 3 | 160 | 2 |
| 123 | 3 | 161 | 0.8 |
| 124 | 2 | 162 | 1 |
| 125 | 2 | 163 | 3 |
| 126 | 3 | 164 | 2 |
| 127 | 2 | 165 | 0.3 |
| 128 | 1 | 166 | 0.5 |

TABLE 3

| Ex.no. | IC$_{50}$ ($\mu$M) in serotonin liberation from RBL-2H3 cells | Ex.no. | IC$_{50}$ ($\mu$M) in serotonin liberation from RBL-2H3 cells |
|---|---|---|---|
| 168 | 2 | 211 | 10 |
| 169 | 0.5 | 212 | 6 |
| 170 | 0.5 | 215 | 3 |
| 171 | 0.8 | 216 | 3 |
| 172 | 3 | 217 | 2 |
| 173 | 0.3 | 220 | 6 |
| 174 | 0.5 | 222 | 10 |
| 175 | 0.8 | 223 | 10 |
| 176 | 2 | 230 | 6 |
| 177 | 1 | 231 | 3 |
| 179 | 2 | 232 | 10 |
| 180 | 2 | 234 | <3 |
| 181 | 2 | 235 | <1 |
| 182 | 2 | 236 | 1 |
| 183 | 3 | 237 | 10 |
| 184 | 0.5 | 239 | 12 |
| 185 | 0.5 | 240 | 5 |
| 186 | 10 | 241 | 4 |
| 188 | 1 | 242 | 6 |
| 189 | 0.8 | 243 | 6 |
| 190 | 0.5 | 244 | 3 |
| 191 | 3 | 247 | 10 |
| 192 | 5 | 248 | 10 |
| 193 | 2 | 249 | 10 |
| 194 | 10 | 251 | 5 |
| 195 | 0.5 | 253 | 10 |
| 196 | 5 | 254 | 12 |
| 197 | 8 | 255 | 8 |
| 199 | 10 | 257 | 12 |
| 200 | 0.4 | 258 | 6 |
| 201 | 10 | 259 | 4 |
| 202 | 6 | 260 | 6 |
| 206 | 15 | 261 | 10 |
| 207 | 15 | 262 | 8 |
| 208 | 3 | | |
| 209 | 15 | | |
| 210 | 10 | | |

The compound numbers correspond to Example Nos. as will be given hereinafter (the same will apply hereinafter).

(2) Inhibitory Effects on Various Mediators Release from Human Basophils i) Experimental Method 6 ml of 6% dextran (for separating leukocytes, having a high molecular weight) was added to 20 ml of heparinized blood. After stirring well, the resulting mixture was allowed to stand at 37° C. for 30 min and thus erythrocytes were precipitated. The upper layer was taken up and phosphate buffered saline (D-PBS) was added thereto followed by centrifugation at 185 g for 8 minutes to give a crude leukocyte fraction. These cells were subjected to hypotonic hematolysis and then suspended in D-PBS(+) containing 0.1%-BSA. The resulting suspension was used in the subsequent experiment as the leukocyte fraction containing basophils. 0.4 ml of this cell suspension was preliminarily heated to 37° C. for 5 min and then 0.05 ml of a specimen solution was added thereto followed by a pretreatment at 37° C. for 15 min. Next, 0.05 ml of a mite antigen solution was added thereto to induce an antigen-antibody reaction. After 10 min, the reaction was ceased by ice-cooling. Then the reaction mixture was centrifuged at 185 g for 10 min and histamine and peptide leukotrienes in the resulting supernatant were determined by using enzyme immunoassay kits. From the results of the assay, the activities of the acridone derivatives of inhibiting the liberation of histamine and peptide leukotriene were determined.

ii) Results of the Experiment

The results are given in Tables 4 to 7 wherein the term "leukotriene" means peptide leukotriene.

TABLE 4

Inhibitory effects on various mediators release from human basophils

| | IC$_{50}$ ($\mu$M) in mediator liberation from human basophils | |
|---|---|---|
| Ex.no. | histamine | leukotriene |
| 22 | 10–30 | 10 |
| 23 | 10–30 | 10–30 |
| 24 | 10–30 | 10–30 |
| 25 | 30 | 10–30 |
| 26 | <10 | <10 |
| 27 | 30–100 | 10–30 |
| 28 | 10–30 | 3 |
| 29 | 10–30 | 3–10 |
| 30 | 3–10 | <3 |
| 32 | 30–100 | 10–30 |
| 33 | 10–30 | 10 |
| 34 | 3–10 | 3 |
| 35 | 3 | 3–10 |
| 36 | 3–10 | 3–10 |
| 37 | 10–30 | 3–10 |
| 39 | 10–30 | 10–30 |

TABLE 4-continued

Inhibitory effects on various mediators release from human basophils

| Ex.no. | IC$_{50}$ ($\mu$M) in mediator liberation from human basophils | |
|---|---|---|
| | histamine | leukotriene |
| 42 | 3–10 | <3 |
| 44 | 10–30 | 10 |
| 45 | 3–10 | 3 |
| 46 | 10–30 | 10–30 |
| 47 | 3–10 | 3 |
| 48 | 3–10 | 3 |
| 49 | 10 | 3–10 |
| 50 | 30 | 10–30 |
| 51 | 10–30 | 10–30 |
| 53 | 30–100 | 10–30 |
| 54 | 10 | 3–10 |
| 58 | 10–30 | 10–30 |

TABLE 5

| Ex.no. | IC$_{50}$ ($\mu$M) in mediator liberation from human basophils | |
|---|---|---|
| | histamine | leukotriene |
| 62 | 10 | 3 |
| 64 | 3–10 | 3 |
| 65 | 30–100 | 10–30 |
| 66 | <3 | <3 |
| 67 | 10–30 | 10–30 |
| 69 | 10 | 3–10 |
| 73 | 3–10 | 3–10 |
| 80 | 10 | 3–10 |
| 81 | 10–30 | 3–10 |
| 82 | 3–10 | 10–30 |
| 83 | 10 | 10–30 |
| 84 | <3 | <3 |
| 85 | 3 | 10–30 |
| 86 | 10–30 | 10 |
| 87 | 3–10 | 3–10 |
| 90 | 30–100 | 10–30 |
| 94 | 30–100 | 10 |
| 100 | 3 | 10 |
| 102 | 30 | 10–30 |
| 105 | 30 | 10–30 |
| 108 | 30 | 10–30 |
| 113 | 10 | <10 |
| 114 | 30–100 | 10 |
| 115 | 30–100 | 10 |
| 122 | 10–30 | <10 |
| 123 | 30 | 10–30 |
| 124 | 10–30 | 10 |
| 125 | <10 | <10 |

TABLE 6

| Ex.no. | IC$_{50}$ ($\mu$M) in mediator liberation from human basophils | |
|---|---|---|
| | histamine | leukotriene |
| 127 | 10–30 | 10 |
| 128 | not done | 10–30 |
| 134 | 3 | 3 |
| 136 | 30–100 | 10–30 |
| 137 | 10–30 | 3 |
| 138 | 10–30 | 10 |
| 139 | 30–100 | 10–30 |
| 140 | 10 | 3–10 |
| 141 | 10–30 | 10–30 |
| 143 | <10 | <10 |

TABLE 6-continued

| Ex.no. | IC$_{50}$ ($\mu$M) in mediator liberation from human basophils | |
|---|---|---|
| | histamine | leukotriene |
| 144 | 10–30 | 10–30 |
| 145 | 10–30 | <10 |
| 146 | <10 | <10 |
| 147 | 10 | <10 |
| 150 | 10–30 | 3–10 |
| 151 | 10–30 | 3–10 |
| 152 | 3–10 | <3 |
| 154 | 10–30 | <10 |
| 155 | 30–100 | 10–30 |
| 156 | 10 | 10 |
| 157 | 30–100 | 10–30 |
| 158 | 30–100 | 10–30 |
| 161 | 3 | 3 |
| 162 | 30–100 | <10 |
| 163 | 10–30 | 10 |
| 164 | 10 | <10 |
| 165 | 10–30 | 3–10 |
| 166 | 10–30 | 3–10 |

TABLE 7

| Ex.no. | IC$_{50}$ ($\mu$M) in mediator liberation from human basophils | |
|---|---|---|
| | histamine | leukotriene |
| 167 | 10 | 3 |
| 168 | <10 | <10 |
| 169 | 30–100 | 10–30 |
| 170 | 10–30 | 3 |
| 171 | 3–10 | 3–10 |
| 173 | 30 | 10 |
| 174 | 10–30 | 10 |
| 175 | 30–100 | 10 |
| 176 | 30–100 | 10–30 |
| 177 | 10 | <3 |
| 179 | 10–30 | 3–10 |
| 180 | 30–100 | 3–10 |
| 181 | 10–30 | <10 |
| 182 | 30–100 | 10–30 |
| 183 | 30–100 | 10–30 |
| 184 | 30–100 | 3–10 |
| 185 | 10–30 | <3 |
| 187 | 10–30 | 3–10 |
| 188 | 10 | 3–10 |
| 189 | 3–10 | 3–10 |
| 190 | 3 | 10 |
| 193 | 30 | 10 |
| 195 | 30–100 | 10–30 |
| 201 | 10 | <10 |
| 202 | 10–30 | <10 |
| 235 | 30 | 30 |

(3) Inhibitory Effects on the Interaction between IgE Receptor γ Chain and 72 kDa Tyrosine Kinase i) Experimental Method RBL-2H3 cells which are a cell line generally used in studying IgE-mediated intracellular signal transduction in mast cells and basophils were used in this study. Tyrosine-phosphorylated peptide in the tyrosine activation motif (TAM) region in the IgE receptor γ chain was synthesized by Peptide Institute.

In the experiment, cell lysates or cytosolic fraction of RBL-2H3 cells were used. Cell lysates were prepared by solubilizing $1\times10^7$ to $5\times10^7$ cells with a solution containing various protease inhibitors and 1%-NP-40 as a solubilizer. Separately, the cells were homogenized in a Downs homogenizer and centrifuged at 50,000 rpm for 1 hr, and the resulting supernatant was used as the cytosol fraction of the cells. The concentration of the lysate or cytosol was adjusted to 1 mg protein/ml with an isotonic buffer. The phosphorylation experiment of the 72 kDa tyrosine kinase contained in the lysate or cytosol was carried out in the following manner.

An assay buffer [150 mM NaCl, 10 mM KCl, 20 mM Tris (pH 7.5), 0.6 mM $MnCl_2$, 0.5 mM EGTA, 5 mM NaF, 1 mM sodium pyrophosphate and 1 mM sodium orthovanadate] containing the lysate or cytosol in an amount corresponding to 10 mg of protein was incubated together with the compound 101 at 30° C. for 3 min. After adding 50 mM of the peptide in the TAM region containing the phosphorylated tyrosine and 50 mM of ATP, the incubation was further effected at 30° C. for 15 min. After the completion of the reaction, the sample was electrophoresed on a 10% agarose gel and a tyrosine kinase of 72 kDa was separated. The activation of this kinase was confirmed by examining the phosphorylation of the tyrosine moiety in the kinase per se by western blotting with the use of anti-tyrosine phosphorylation antibody. Then the extent of the phosphorylation was numerically expressed by using an image analyzer and thus the tyrosine kinase phosphorylation inhibitory ratio of the compound 101 was determined.

ii) Results of the Experiment

The results are given in Table 8.

(4) Effect of Inhibiting Activation (Phosphorylation) of Tyrosine Kinase of 72 kDa Due to Antigenic Stimulation in RBL-2H3 Cells i) Experimental Method RBL-2H3 cells were incubated for 10 min together with a test compound in a PBS buffer containing 0.1% of BSA and 1 mM of calcium. Next, the cells were reacted with an antigen specific for the IgE receptor for 10 min. After the completion of the antigenic stimulation, the cells were allowed to stand in ice for 1 hr in a 10 mM phosphate buffer (pH 7.5) containing a lysis buffer (1% Triton X-100, 0.1% SDS, 0.5% sodium deoxycholate, 50 mM NaCl, 50 mM NaF, 1 mM phenylmethyl sulfonyl fluoride, 50 µg/ml eupeptin, 10 unit/ml aprotonin) and 0.1% of $NaN_3$ followed by centrifugation to give a cell lysate. This lysate was diluted with a buffer for electrophoresis, heated (95° C., 5 min) and then electrophoresed on a 10% SDS-polyacrylamide gel. After the electrophoresis, the sample was electrically transcribed onto a 0.2 µm nitrocellulose membrane and treated with an anti-phosphotyrosine antibody for 1 hr. Then the inhibitory activity was evaluated by the coloring analysis through chemiluminescence.

ii) Results of the Experiment

The results are given in Table 9.

These results indicate that the compounds of the present invention would inhibit the binding of the IgE receptor γ chain to the tyrosine kinase of 72 kDa and thus suppress the liberation of chemical mediators such as serotonin, histamine and leukotrienes.

Therefore, the compounds of the present invention are usable as preventives or remedies for diseases against which the effect of inhibiting binding of the IgE receptor γ chain to a tyrosine kinase of 72 kDa is efficacious. More particularly speaking, the compounds of the present invention are usable as preventives or remedies for diseases caused by the liberation of chemical mediators such as serotonin, histamine and leukotrienes. Still particularly, these compounds are useful in preventing or treating allergic diseases such as asthma, allergic rhinitis, atopic dermatitis, urticaria, hay fever, gastrointestinal allergy or food allergy.

Moreover, the compounds of the present invention are useful from the viewpoint the low toxicity and high safety thereof.

When the compounds of the present invention are used for the above-mentioned diseases, they may be administered both orally and parenterally in the dosage form of tablets, powders, granules, capsules, syrups, troches, inhalants, suppositories, injections, ointments, ophthalmic ointments, eye drops, nasal drops, ear drops, cataplasmas, lotions, etc.

The administration dose widely varies depending on the type of the disease, the severity of the symptoms, the age, sex and drug sensitivity of the patient. In general, such a compound is administered in a daily dose of from about 0.03 to 1,000 mg, preferably from 0.1 to 500 mg and still preferably from 0.1 to 100 mg once to several times a day. In the case of injections, the dose usually ranges from about 1 µg/kg to 3,000 µg/kg, preferably from about 3 µg/kg to 1,000 µg/kg.

The compounds of the present invention may be processed into preparations by conventional methods with the use of conventional pharmaceutical carriers.

Namely, solid preparations for oral administration are prepared by mixing the principal agent with fillers, binders, disintegrating agents, lubricants, coloring agents, corrigents, antioxidants, etc. and then processed into tablets, coated tablets, granules, powders, capsules, etc. by conventional methods.

Examples of the above-mentioned fillers are lactose, corn starch, sucrose, glucose, sorbitol, crystalline cellulose, silicon dioxide, etc.

Examples of the binders are polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin. Examples of the lubricants are magnesium stearate, talc, polyethylene glycol, silica, hardened vegetable oils, etc.

The coloring agents are those admitted to be added to medicines. Examples of the corrigents include cocoa powder, menthol, aromatic powder, peppermint oil, borneol and powdered cinnamon bark. As the antioxidants, use can be made of any pharmaceutically authorized ones such as ascorbic acid and α-tocopherol. Needless to say, tablets and granules may be appropriately coated with sugar, gelatin, etc., if necessary.

Meanwhile, injections, eye drops, etc. can be prepared by blending the principal agent with, if needed, pH regulating agents, buffer agents, suspending agents, dissolution aids, stabilizers, tonicity agents, antioxidants, preservatives, etc. and then processed in a conventional manner. In such a case, it is also possible, if needed, to give freeze-dried preparations. Injections may be intravenously, hypodermically or intramuscularly administered.

Examples of the above-mentioned suspending agents include methylcellulose, Polysorbate 80, hydroxyethylcellulose, acacia, tragacanth, sodium carboxymethylcellulose and polyoxyethyelne sorbitan monolaurate.

Examples of the dissolution aids are polyoxyethylene-hardened castor oil, Polysorbate 80, nicotinamide, polyoxyethylene sorbitan monolaurate, etc.

Examples of the stabilizers usable herein include sodium sulfite, sodium metasulfite and ether. Examples of the preservatives usable herein include methyl p-hydroxybenzoate, ethyl p-hydroxybenzoate, sorbic acid, phenol, cresol and chlorocresol.

Ointments can be produced by blending the principal agent with, if needed, stabilizers, antioxidants, preservatives, etc. and processed in a conventional manner.

EXAMPLES

To illustrate the present invention, the following Examples will be given, though it is needless to say that the present invention is not restricted thereto. Analogous compounds synthesized by similar procedures are listed in tables. The synthesized sulfoxide compounds are all mixtures of optical isomers. The ¹H-NMR data sometimes do not involve active hydrogen in the compounds. In the table, each number given at the lower left of the structural formula means the Example number. Prior to the Examples of the compounds of the present invention, Production Examples of the starting compounds will be given.

Production Example 1
1,2-Dimethyl-10-(3-chloropropyl)phenothiazine

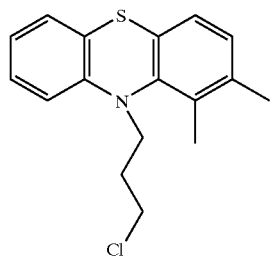

To a solution of 5.0 g of 1,2-dimethylphenothiazine in N,N'-dimethylformamide was added 970 mg of sodium hydride under stirring at room temperature. After stirring at room temperature for 30 min, 4.0 g of 1-chloro-3-iodopropane was added dropwise followed by stirring at room temperature overnight. After adding water, the reaction mixture was extracted with ethyl acetate. The organic layer was washed with water and dried over anhydrous magnesium sulfate. After evaporating the solvent under reduced pressure, the residue was purified by silica gel column chromatography to give 3.4 g of the title compound.

¹H-NMR, (400 MHz, CDCl₃) δ 7.18–7.14(m, 2H), 7.11–7.07(m, 1H), 6.09–6.94(m, 1H), 6.92(d, J=8, 1H), 6.85(d, J=8, 1H), 4.00–3.90(m, 1H), 3.80–3.60(m, 1H), 3.62–3.55(m, 2H), 2.55(s, 3H), 2.50 (S, 3H), 2.06–1.96(m, 2H).

Production Example 2
1,2-Dimethyl-10-(3-phthalimdopropl)phenothiazine

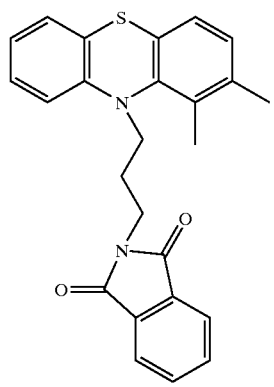

3.4 g of 1,2-dimethyl-10-(3-chloropropyl)phenothiazine obtained in Production Example 1 and 6.2 g of potassium phthalimide were dissolved in 100 ml of N,N'-dimethylformamide and stirred at 60° C. for 40 hr. After adding water, the reaction mixture was extracted with ethyl acetate. The organic layer was washed with water and dried over anhydrous magnesium sulfate. After evaporating the solvent under reduced pressure, the residue was purified by silica gel column chromatography to give 4.4 g of the title compound.

¹H-NMR, (400 MHz, CDCl₃) δ 7.82–7.76(m, 2H), 7.70–7.65(m, 2H), 7.16–7.08(m, 3H), 6.98–6.93(m, 1H), 6.89(d, J=8, 1H), 6.82(d, J=8, 1H), 3.85–3.72(m, 2H), 3.68(t, J=7, 2H), 2.25(s, 3H), 2.21 (S, 3H), 2.02–1.85(m, 2H).

Production Example 3
1,2-Dimethyl-10-(3-chloropropyl)phenothiazine-5-oxide

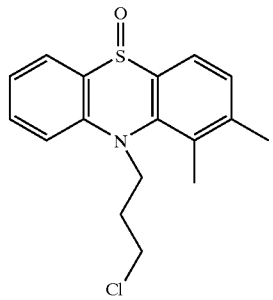

21.3 g of 1,2-dimethyl-10-(3-chloropropyl)phenothiazine obtained in Production Example 1 was dissolved in dichloromethane and 18.0 g of 3-chlorobenzoic acid was added thereto at 0° C. After stirring at the same temperature for 1 hr, the reaction mixture was poured into a saturated aqueous solution of sodium bicarbonate and extracted with ethyl acetate. The organic layer was washed with water and dried over anhydrous magnesium sulfate. After evaporating the solvent under reduced pressure, the residue was purified by silica gel column chromatography to give 13.05 g of the title compound.

¹H-NMR, (400 MHz, CDCl₃) δ 7.78(d, J=8, 1H), 7.59(d, J=8, 1H), 7.56–7.52(m, 2H), 7.23–7.17(m, 1H), 7.15(d, J=8, 1H), 4.43(m, 1H), 4.19(m, 1H), 3.54–3.43(m, 2H), 2.42 (s, 3H), 2.39(s, 3H), 2.11–1.93 (m, 2H).

Production Example 4
1,2-Dimethyl-10-(3-phthalimidopropyl)phenothiazine-5-oxide

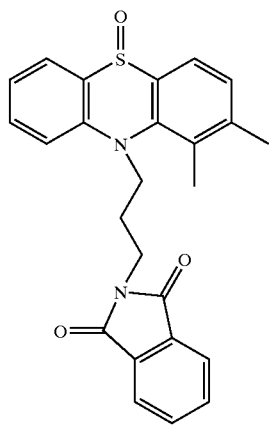

To a solution of 1.25 g of 1,2-dimethyl-10-(3-phthalimidopropyl)phenothiazine obtained in Production Example 2 in methylene chloride (15 ml) was added under ice cooling 510 mg of 3-chloroperbenzoic acid and the mixture was stirred under ice cooling for 1 hr. After adding water, the reaction mixture was extracted with dichloromethane. The organic layer was washed with a saturated aqueous solution of sodium bicarbonate and an aqueous solution of sodium chloride and then dried over anhydrous magnesium sulfate. After evaporating the solvent under reduced pressure, the residue was purified by silica gel column chromatography to give 1.19 g of the title compound.

$^1$H-NMR, (400 MHz, CDCl$_3$) δ 7.81–7.79(m, 2H), 7.78–7.75(m, 1H), 7.70–7.68(m, 2H), 7.56(d, J=8, 1H), 7.51–7.45(m, 2H), 7.21–7.17(m, 1H), 7.13(d, J=8, 1H), 4.30–4.18(m, 1H), 4.07–3.99(m, 1H), 3.62 (t, J=7, 2H), 2.36(S, 6H), 1.94–1.88(m, 2H).

Production Example 5

1,2-Dimethyl-10-[2-(2-tetrahydropyranyloxy)ethyl]phenothiazine

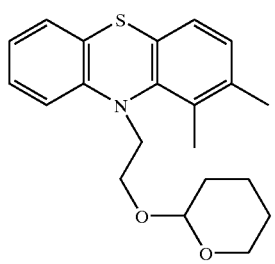

The procedure of Production Example 1 was repeated while using 1-iodo-2-(2-tetrahydropyranyloxy)ethane instead of 1-chloro-3-iodopropane to give the title compound.

$^1$H-NMR, (400 MHz, CDCl$_3$) δ 7.15–7.10(m, 3H), 6.98–6.92(m, 1H), 6.90(d, J=8, 1H), 6.83(d, J=8, 1H), 4.49–4.44(m, 1H), 4.04–3.65(m, 4H), 3.58–3.48(m, 1H), 3.43–3.36(m, 1H), 2.28(s, 3H), 2.23(s, 3H), 1.75–1.63(m, 1H), 1.63–1.35(m, 4H), 1.35–1.20(m, 1H).

Production Example 6

1,2-Dimethyl-10-(2-hydroxyethyl)phenothiazine

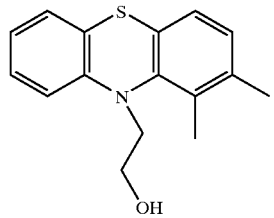

2.2 g of 1,2-dimethyl-10-[2-(2-tetrahydropyranyloxy)ethyl]phenothiazine obtained in Production Example 5 was dissolved in 50 ml of ethanol. After adding a catalytic amount of pyridinium p-toluenesulfonate, the mixture was stirred at 50° C. for 2 hr. After evaporating the solvent under reduced pressure, the residue was purified by silica gel column chromatography to give 1.45 g of the title compound.

$^1$H-NMR, (400 MHz, CDCl$_3$) δ 7.24–7.16(m, 2H), 7.13 (d, J=8, 1H), 7.00(d, J=8, 1H), 6.98(d, J=8, 1H), 6.96(d, J=8, 1H), 4.08(m, 1H), 3.83–3.72(m, 1H), 3.68–3.56(m, 1H), 3.56–3.45(m, 1H), 2.79(t, J=6, 1H), 2, 28(s, 3H), 2.25(s, 3H).

Production Example 7

1,2-Dimethyl-10-(2-phthalimidoethyl)phenothiazine

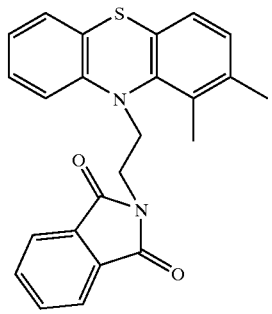

1.45 g of 1,2-dimethyl-10-(2-hydroxyethyl)phenothiazine obtained in Production Example 6, 1.42 g of triphenylphosphine and 0.8 g of phthalimide were dissolved in 20 ml of dry tetrahydrofuran. After adding 0.85 ml of diethyl azodicarboxylate at 0° C., the reaction mixture was stirred at room temperature for 12 hr. After adding water, the reaction mixture was extracted with ethyl acetate. The organic layer was washed with water and then dried over anhydrous magnesium sulfate. After evaporating the solvent under reduced pressure, the residue was purified by silica gel column chromatography to give 1.95 g of the title compound.

$^1$H-NMR, (400 MHz, CDCl$_3$) δ 7.80–7.73(m, 2H), 7.70–7.65(m, 2H), 7, 20(m, 2H), 7.14(d, J=7, 1H), 7.01–6.94(m, 1H), 6.84(d, J=8, 1H), 6.80(d, J=8, 1H), 4.11–3.81(m, 4H), 2, 24(s, 3H), 2.23(s, 3H).

Production Example 8

1,2-Dimethyl-10-(2-bromoethyl)phenothiazine

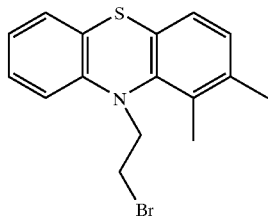

0.5 g of 1,2-dimethyl-10-(2-hydroxyethyl)phenothiazine obtained in Production Example 6, 0.58 g of triphenylphosphine and 0.9 g of carbon tetrabromide were dissolved in 10 ml of dichloromethane followed by stirring at room temperature for 1.5 hr. Then the reaction mixture was purified by silica gel column chromatography to give 0.55 g of the title compound.

$^1$H-NMR, (400 MHz, CDCl$_3$) δ 7.20–7.18(m, 3H), 7.02 (m, 1H), 6.93(d, J=8, 1H), 6.89(d, J=8, 1H), 4.01(m, 1H), 3.80(m, 1H), 3.40(m, 2H), 2.30(s, 3H), 2.23(s, 3H).

Production Example 9

3,4-Dimethyl-9-methylene-10-(3-bromopropyl)acridan 0.1 g of 3,4-dimethyl-10-(3-bromopropyl)-9-acridone was dissolved in 5 ml of dry tetrahydrofuran. Then 0.36 ml of methyllithium (a 1.4 M solution in diethyl ether) was added dropwise at −78° C. After stirring at the same temperature for 1 hr, water was added to the liquid reaction mixture followed by extraction with ethyl acetate. The organic layer was washed with water and dried over anhydrous magnesium sulfate. After evaporating the solvent under reduced pressure, the residue was purified by silica gel column chromatography to give 0.1 g of the title compound.

$^1$H-NMR, (400 MHz, CDCl$_3$) δ 7.54(dd, J=8, 1, 1H), 7.33(d, J=8, 1H), 7, 28(m, 1H), 7.23(dd, J=8, 1, 1H), 7.04(m, 1H), 6.95(d, J=8, 1H), 5.39(s, 1H), 5.30 (s, 1H), 3.95 (t, J=7, 2H), 3.12 (t, J=7, 2H), 2.33(s, 3H), 2.30(s, 3H), 1.81(m, 2H).

Production Example 10
3,4-Dimethyl-9-chloro-10-(3-phthalimidopropyl) acridinium Chloride A mixture of 1.0 g of 3,4-dimethyl-10-(3-phthalimidopropyl)-9-acridone with 340 ml of oxalyl chloride was stirred at room temperature in 100 ml of dichloromethane for 30 min. After evaporating the excessive oxalyl chloride and dichloromethane under reduced pressure, 1.1 g of the title compound was obtained.

Production Example 11
(E,Z)-3,4-Dimethyl-10-(3-phthalimidopropyl)-9-acridoneoxime-O-methyl Ether 1.1 g of 3,4-dimethyl-9-chloro-10-(3-phthalimidopropyl) acridinium chloride obtained in Production Example 10 was dissolved in 50 ml of acetonitrile. After adding 250 mg of methoxamine hydrochloride, the resulting mixture was stirred at room temperature for 20 min. After adding water, the reaction mixture was extracted with ethyl acetate. The organic layer was washed with brine and dried over anhydrous magnesium sulfate. After evaporating the solvent under reduced pressure, the residue was purified by silica gel column chromatography to give 480 mg of the title compound as a mixture of the E- and Z-enantiomers (1:1).

$^1$H-NMR, (400 MHz, CDCl$_3$) δ 8.42(dd, J=8, 2, 0.5H), 8.28(d, J=8, 0.5H), 7.80–7.76(m, 2.5H), 7.68–7.66(m, 2H), 7.58(d, J=8, 0.5H), 7.36–7.21(m, 2H), 7.06–7.02(m, 1H), 7.14(d, J=8, 1H), 4.05(s, 1.5H), 4.04(s, 1.5H), 4.00–3.90(m, 2H), 3.48(t, J=7, 2H), 2.31–2.28(m, 6H), 1.70–1.60(m, 2H).

Production Example 12
2-(Nitrophenyl)amino-3,4-dimethylbenzoic Acid 10 g of 3,4-dimethyl-2-iodobenzoic acid, 6 g of 2-nitroaniline, 250 mg of powdery copper and 25 g of potassium carbonate were added to N,N-dimethylformamide and heated under reflux while stirring for 2 hr. Then the reaction mixture was cooled to room temperature and diluted with water. After adjusting the pH value thereof to pH 4 with conc. hydrochloric acid, it was extracted with ethyl acetate. The organic layer was washed with brine and dried over anhydrous magnesium sulfate. After evaporating the solvent under reduced pressure, the residue was purified by silica gel column chromatography to give 2.5 g of the title compound.

$^1$H-NMR, (400 MHz, CDCl$_3$) δ 8.13(dd, J=8, 1, 1H), 7.84(d, J=8, 1H), 7.26(m, 1H), 7.13(d, J=8, 1H), 6.72(m, 1H), 6.36(dd, J=8, 1, 1H), 2.36(s, 3H,) 2.03(s, 3H).

Production Example 13
5,11-Dihydro-3,4-dimethyl-11-oxo-10H-dibenzo[b,e]-1,4-diazepine 2.5 g of 2-(nitrophenyl)amino-3,4-dimethylbenzoic acid obtained in Production Example 12 was dissolved in 47.4 ml of methanol and 94.7 ml of a 2 N aqueous ammonia and 1.44 g of sodium hydrosulfite were added thereto. After stirring at room temperature overnight, water was added to the reaction mixture and the pH value of the mixture was adjusted to pH 4 with conc. hydrochloric acid. After extracting with ethyl acetate, the organic layer was washed with brine and dried over anhydrous magnesium sulfate. After evaporating the solvent under reduced pressure, the residue was dissolved in 100 ml of xylene and heated under reflux for 2 hr. After cooling, the solvent was evaporating and the residue was purified by silica gel column chromatography to give 850 mg of the title compound.

$^1$H-NMR, (400 MHz, CDCl$_3$) δ 7.84(s, 1H), 7.68(d, J=8, 1H), 7.05–6.97(m, 2H), 6.93–6.87(m, 2H), 6.85(d, J=8, 1H), 5.62(s, 1H), 2.31(s, 3H), 2.30(s, 3H)

Production Example 14
5,11-Dihydro-3,4,10-trimethyl-11-oxo-10H-dibenzo[b,e]-1,4-diazepine 850 mg of 5,11-dihydro-3,4-dimethyl-11-oxo-10H-dibenzo[b,e]-1,4-diazepine obtained in Production Example 13 was dissolved in 15 ml of tetrahydrofuran and 3.75 ml of a 1 M solution of bis(trimethylsilyl)lithiumamide in tetrahydrofuran was added thereto. After stirring at room temperature for 10 min, 0.27 ml of iodomethane was added thereto and the resulting mixture was stirred at room temperature for 1 hr. After adding water, the reaction mixture was extracted with ethyl acetate. The organic layer was washed with brine and dried over anhydrous magnesium sulfate. After evaporating the solvent under reduced pressure, the residue was purified by silica gel column chromatography to give 540 mg of the title compound.

$^1$H-NMR, (400 MHz, CDCl$_3$) δ 7.61(d, J=8, 1H), 7.18(dd, J=8, 2, 1H), 7.09(m, 1H), 7.04(m, 1H), 6.92(dd, J=8, 2, 1H), 6.85(d, J=8, 1H), 5.62(s, 1H), 3.54(s, 3H), 2.30(s, 6H).

Production Example 15
5-(3-Bromopropyl)-5,11-dihydro-3,4,10-trimethyl-11-oxo-10H-dibenzo[b,e]-1,4-diazepine

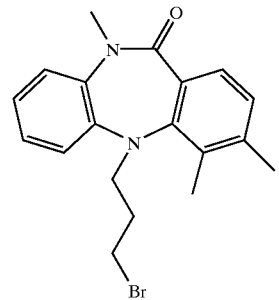

800 mg of 5,11-dihydro-3,4,10-trimethyl-11-oxo-10H-dibenzo[b,e]-1,4-diazepine obtained in Production Example 14 was dissolved in 20 ml of tetrahydrofuran and 1.7 ml of a 2.5 M solution of n-butyllithium in hexane was added thereto at −40° C. Then the internal temperature was warmed to 10° C. over 20 min and 1.24 g of 3-bromo-1-propanol trifluoromethanesulfonate was added thereto followed by stirring at room temperature for 30 min. After adding water, the reaction mixture was extracted with ethyl acetate. The organic layer was washed with brine and dried over anhydrous magnesium sulfate. After evaporating the solvent under reduced pressure, the residue was purified by silica gel column chromatography to give 830 mg of the title compound.

¹H-NMR, (400 MHz, CDCl₃) δ 7.56(d, J=8, 1H), 7.30(dd, J=8, 2, 1H), 7.24–7.18(m, 2H), 7.15–7.09(m, 1H), 704(d, J=8, 1H), 3.63–3.49(m, 2H), 3.60(s, 3H), 3.48–3.39(m, 2H), 2.39(s, 3H), 2.28(s, 3H), 2.03–1.94(m, 2H).

Example 1
1,2-Dimethyl-10-(3-aminopropyl)phenothiazine

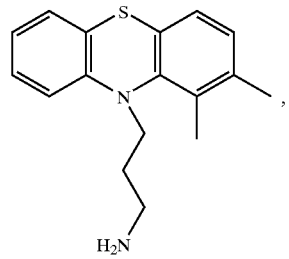

100 ml of a solution of 1.6 g of 1,2-dimethyl-10-(3-phthalimidopropyl)phenothiazine obtained in Production Example 2 and 2.0 ml of hydrazine monohydrate in methanol was stirred under reflux for 4 hr. After evaporating the solvent under reduced pressure, the residue was basified with a 1 N aqueous solution of sodium hydroxide and extracted with dichloromethane. The organic layer was washed with brine and dried over anhydrous magnesium sulfate. After evaporating the solvent under reduced pressure, the residue was purified by silica gel column chromatography to give 870 mg of the title compound.

¹H-NMR, (400 MHz, CDCl₃) δ 7.16–7.12(m, 2H), 7.08 (dd, J=1.2, 8, 1H), 6.97–6.92(m, 1H), 6.90(d, J=8, 1H), 6.83(d, J=8, 1H), 3.90–3.78(m, 1H), 3.66–3.50(m, 1H), 2.69(t, J=7, 2H), 2.25(s, 3H), 2.23(s, 3H), 1.76–1.68(m, 2H).

The following compounds were obtained by the same procedure as the one of Example 1.

Example 4
1,2-Dimethyl-10-(3-benzylaminopropyl)phenothiazine

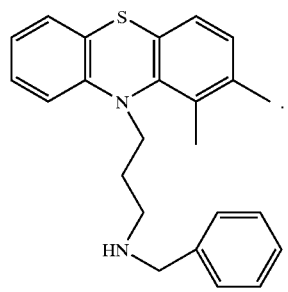

The procedure of Production Example 1 was repeated while using 3-bromopropyl trifluoromethanesulfonate instead of 1-chloro-3-iodopropane to give 1,2-dimethyl-10-(3-bromopropyl)phenothiazine. 50 ml of a solution of 400 mg of the resulting compound and 370 mg of benzylamine in ethanol was stirred at 70° C. for 30 min. Then the reaction mixture was cooled to room temperature and a saturated aqueous solution of sodium bicarbonate was added thereto. After extracting with ethyl acetate, the organic layer was washed with brine and dried over anhydrous magnesium sulfate. After evaporating the solvent under reduced pressure, the residue was purified by silica gel column chromatography to give 40 mg of the title compound.

¹H-NMR, (400 MHz, CDCl₃) δ 7.30–7.10(m, 7H), 7.07–7.04(m, 1H), 6.96–6.91(m, 1H), 6.88(d, J=8, 1H), 6.82(d, J=8, 1H), 3.90–3.80(m, 1H), 3.67(s, 2H), 3.64–3.54 (m, 1H), 2.66(t, J=7, 2H), 2.23(s, 3H), 2.22 (s, 3H), 1.84–1.76(m, 2H).

The following compounds were obtained by the same procedure as the one of Example 4.

TABLE 10

| Ex. no. | | ¹H-NMR (400 MHz) δ |
|---|---|---|
| 2 | (structure: 7-bromo-1,2-dimethyl-10-(3-aminopropyl)phenothiazine) | CDCl₃<br>7.20(d, J=2, 1H), 7.06(dd, J =2, 8, 1H), 6.98(d, J=8, 1H), 6.89(d, J=8, 1H), 6.84(d, J=8, 1H), 3.90–3.78(m, 1H), 3.64–3.50(m, 1H), 2.67(t, J=7, 2H), 2.23(s, 6H), 1.75–1.68(m, 2H) |
| 3 | (structure: phenothiazine with pyridylmethyl-aminomethyl substituent) | CDCl₃<br>7.43(t, J=8, 1H), 7.35(d, J=8, 1H), 7.10–6.98(m, 4H), 6.92–6.80(m, 3H), 5.20–4.80(m, 2H), 3.68(s, 2H), 2.35(s, 3H), 2.23(s, 3H) |

TABLE 11

| Ex. no. | | ¹H-NMR (400 MHz) δ |
|---|---|---|
| 5 | 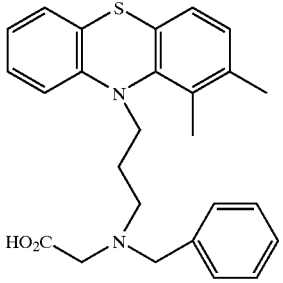 | CDCl₃<br>7.34–7.26(m, 3H), 7.17–7.11(m, 4H), 7.03(dd, J=1, 8, 1H), 6.97–6.93(m, 1H), 6.87(d, J=8, 1H), 6.84(d, J=8, 1H), 3.96–3.88(m, 1H), 3.82(s, 2H), 3.60–3.46(m, 1H), 3.18(s, 2H), 3.00–2.80(m, 2H), 2.23(s, 3H), 2.20(s, 3H), 1.90–1.78(m, 2H) |
| 6 | 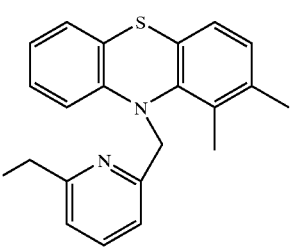 | CDCl₃<br>7.45(t, J=8, 1H), 7.38(d, J=8, 1H), 7.35–7.23(m, 5H), 7.08–6.98(m, 4H), 6.90–6.80(m, 3H), 5.20–4.80(m, 2H), 3.82(s, 2H), 3.75(s, 2H), 2.35(s, 3H), 2.23(s, 3H) |
| 7 | 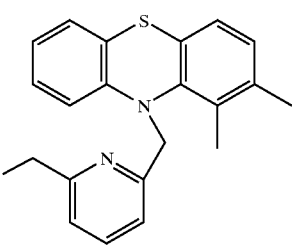 | CDCl₃<br>7.47(t, J=8, 1H), 7.26(d, J=8, 1H), 7.11–7.01(m,.4H), 6.95(s, 2H), 6.88–6.79(m, 3H), 5.20–4.80(m, 2H), 3.83(s, 2H), 3.77(s, 2H), 2.37(s, 3H), 2.21(s, 3H) |

Example 8

1,2-Dimethyl-10-(3-aminopropyl)phenothiazine-5-oxide 50 ml of a solution of 1.19 g of 1,2-dimethyl-10-(3-phthalimidopropyl)phenothiazine-5-oxide obtained in Production Example 4 and 1.5 ml of hydrazine monohydrate in methanol was stirred at 40° C. for 2 hr. After evaporating the solvent, the residue was extracted with dichloromethane. After evaporating the solvent under reduced pressure, 700 mg of the title compound was obtained.

¹H-NMR, (400 MHz, CDCl₃) δ 7.75(dd, J=1, 8, 1H), 7.72–7.68(m, 1H), 7.60–7.55(m, 1H), 7.55(d, J=8, 1H), 7.22–7.16(m, 2H), 4.36–4.26(m, 1H), 4.02–3.92(m, 1H), 2.39(t, J=7, 2H), 2.34(s, 3H), 2.33(s, 3H), 1.45–1.38(m, 2H).

The following compounds were obtained by the same procedure as the one of Example 8.

TABLE 12
| Ex. no. | | $^1$H-NMR (400 MHz) δ |
|---|---|---|
| 9 | 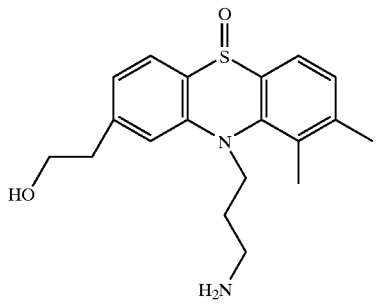 | DMSO-d6<br>7.64(d, J=8, 1H), 7.55–7.53(m, 2H), 7.15(d, J=8, 1H), 7.06(dd, J=1, 8, 1H), 4.36–4.26(m, 1H), 4.00–3.90(m, 1H), 3.65(t, J=7, 2H), 2.80(t, J=7, 2H), 2.39(t, J=7, 2H), 2.34(s, 3H), 2.32(s, 3H), 1.50–1.32(m, 2H) |
| 10 | 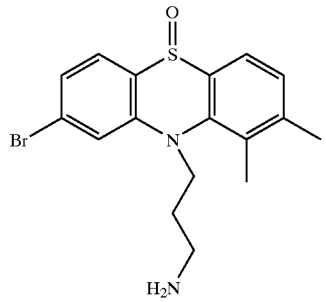 | CDCl$_3$<br>7.64(d, J=2, 1H), 7.62(d, J=8, 1H), 7.56(dd, J=8, 2, 1H), 7.30(dd, J=2, 8, 1H), 7.15(d, J=8, 1H), 4.28–4.18(m, 1H), 4.06–3.98(m, 1H), 2.61(t, J=7, 2H), 2.37(s, 6H), 1.72-1.50(m, 2H) |
| 11 | 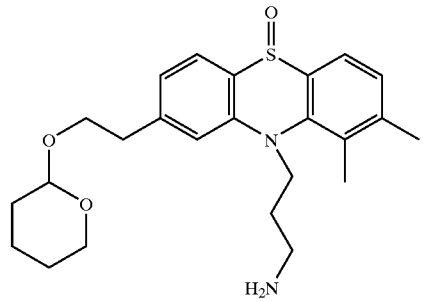 | CDCl$_3$<br>7.66(d, J=8, 1H), 7.54(d, J=8, 1H), 7.40(dd, J=1, 6, 1H), 7.11(d, J=8, 1H), 7.08–7.05(m, 1H), 4.61–4.56(m, 1H), 4.40–4.30(m, 1H), 4.05–3.96(m, 2H), 3.81–3.70(m, 1H), 3.69–3.60(m, 1H), 3.50–3.40(m, 1H), 2.98(t, J=7, 2H), 2.66–2.56(m, 2H), 2.37(s, 3H), 2.36(s, 3H), 1.84–1.64(m, 4H), 1.60–1.40(m, 4H) |
| 12 | 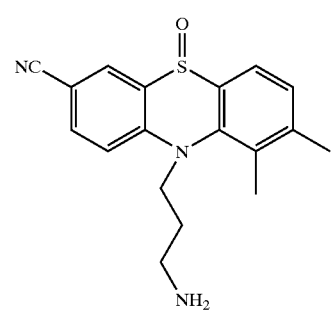 | DMSO-d6<br>8.40(d, J=2, 1H) 8.01(dd, J=2, 8, 1H), 7.91(d, J=8, 1H), 7.66(d, J=8, 1H), 7.27(d, J=8, 1H), 4.58–4.47(m, 1H), 4.12–4.03(m, 1H), 2.43(t, J=7, 2H), 2.37(s, 6H), 1.53–1.37(m, 2H) |
| 13 | 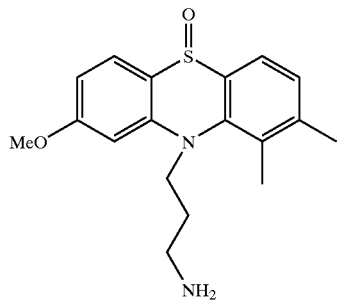 | DMSO-d6<br>7.70(d, J=8, 1H), 7.56(d, J=8, 1H), 7.23(d, J=2, 1H), 7.17(d, J=8, 1H), 6.80(dd, J=2, 8, 1H), 4.48–4.35(m, 1H), 4.00–3.88(m, 1H) 3.88(s, 3H), 2.40–2.28(m, 2H), 2.36(s, 3H), 2.35(s, 3H), 1.65–1.43(m, 2H) |

TABLE 12-continued
| Ex. no. | | $^1$H-NMR (400 MHz) δ |
|---|---|---|
| 14 | 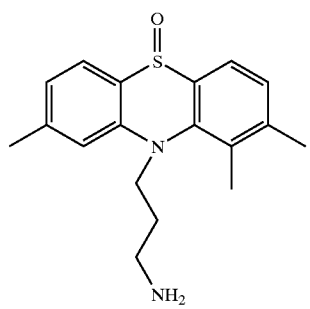 | DMSO-d6<br>7.64(d, J=8, 1H), 7.56(d, J=8, 1H), 7.55(s, 1H), 7.17(d, J=8, 1H), 7.03(d, J=8, 1H), 4.40–4.27(m, 1H), 4.02–3.91(m, 1H), 2.46–2.38(m, 2H), 2.42(s, 3H), 2.35(s, 3H), 2.34(s, 3H), 1.56–1.37(m, 2H) |
| 15 | 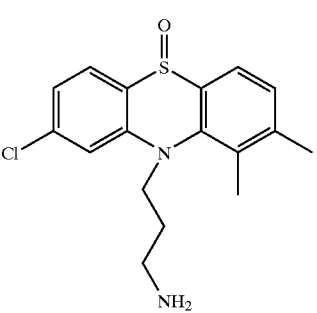 | DMSO-d6<br>7.88(d, J=2, 1H), 7.80(d, J=8, 1H), 7.59(d, J=8, 1H), 7.26(dd, J=2, 8, 1H), 7.22(d, J=8, 1H), 4.46–4.32(m, 1H), 4.05–3.95(m, 1H), 2.48–2.40(m, 2H), 2.36(s, 3H), 2.35(s, 3H), 1.52–1.38(m, 2H) |
TABLE 13
| Ex. no. | | $^1$H-NMR (400 MHz) δ |
|---|---|---|
| 16 | 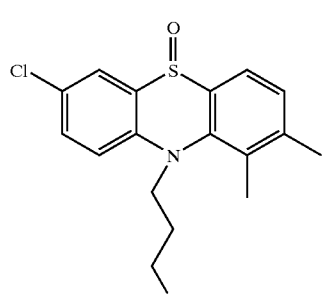 | CDCl$_3$<br>7.74(d, J=2, 1H), 7.57(d, J=8, 1H), 7.46–7.40(m, 2H), 7.15(d, J=8, 1H), 4.20(m, 1H), 4.00(m, 1H), 2.59(t, J=7, 2H), 2.38(s, 3H), 2.38(s, 3H), 1.64(m, 2H) |
| 17 | 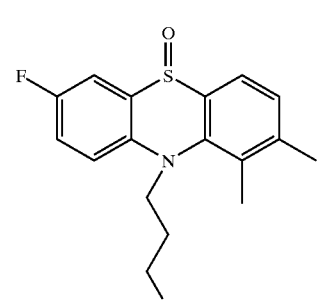 | CDCl$_3$<br>7.56(d, J=8, 1H), 7.50–7.42(m, 2H), 7.21(m, 1H), 7.15(d, J=8, 1H), 4.12(m, 1H), 4.00(m, 1H), 2.59(t, J=7, 2H), 2.38(s, 3H), 2.37(s, 3H), 1.62(m, 2H) |

TABLE 13-continued
| Ex. no. | | $^1$H-NMR (400 MHz) δ |
|---|---|---|
| 18 | 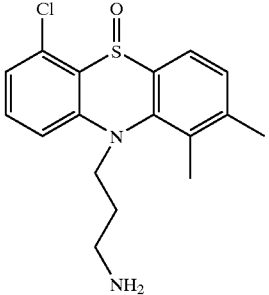 | CDCL$_3$<br>7.62(d, J=8, 1H), 7.46–7.38(m, 2H), 7.18–7.12(m, 2H), 4.40(m, 1H), 4.00(m, 1H), 2.61(m, 2H), 2.39(s, 3H), 2.38(s, 3H), 1.70(m, 2H) |
| 19 | 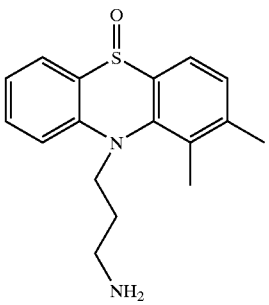 | DMSO-d6<br>8.11(dd, J=2, 8, 1H), 7.74(d, J=8, 1H), 7.63–7.59(m, 1H), 7.20–7.16(m, 1H), 7.04(s, 1H), 4.51–4.42(m, 1H), 3.92–3.82(m, 1H), 2.63(s, 3H), 2.48–2.37(m, 2H), 2.32(s, 3H), 2.30(s, 3H), 1.55–1.38(m, 2H) |
| 20 | 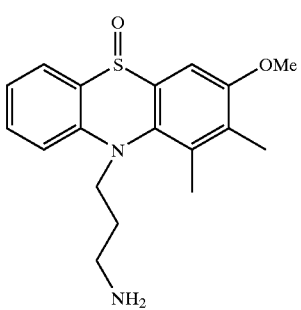 | CDCl$_3$<br>7.76(m, 1H), 7.50–7.44(m, 2H), 7.18(m, 1H), 7.15(s, 1H), 4.17(m, 1H), 3.95(m, 1H), 3.90(s, 3H), 2.58(t, J=7, 2H), 2.39(s, 3H), 2.22(s, 3H), 1.60(m, 2H) |
| 21 | 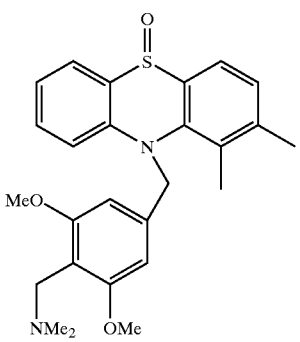 | 7.68(dd, J=8, 2, 1H), 7.60(d, J=8, 1H), 7.28–7.35(m, 2H), 7.15 (d, J=9, 1H), 7.15(d, J=8, 1H), 7.08(m, 1H), 6.47(d, J=9, 1H), 5.33(d, J=15, 1H), 5.11(d, J=15, 1H), 3.72(s, 3H), 3.69(s, 3H), 3.45(d, J=12, 1H), 3.36(d, J=12, 1H), 2.49(s, 3H), 2.37(s, 3H), 2.16(s, 6H) |

Example 22

1,2-Dimethyl-10-(3-benzylaminopropyl)-phenothiazine-5-oxide

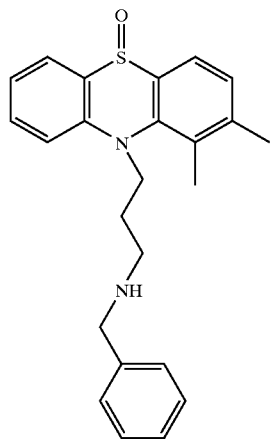

A solution of 1.5 g of 1,2-dimethyl-10-(3-aminopropyl)phenothiazine-5-oxide obtained in Example 8 and 580 mg of benzaldehyde in 60 ml of toluene was stirred under reflux for 2 hr while using a water separator. Then the mixture was cooled to room temperature and the solvent was evaporated under reduced pressure. After adding 60 ml of ethanol and sodium borohydride successively, the reaction mixture was stirred under ice cooling for 10 min. After adding water, the mixture was extracted with ethyl acetate. The organic layer was washed with brine and dried over anhydrous magnesium sulfate. After evaporating the solvent under reduced pressure, the residue was washed with diethyl ether to give 1.9 g of the title compound.

$^1$H-NMR, (400 MHz, CDCl$_3$) δ 7.82(d, J=7, 1H), 7.76(d, J=8, 1H), 7.65–7.60(m, 2H), 7.35(s, 5H), 7.25–7.20(m, 2H), 4.45–4.56(m, 1H), 4.03–3.96(m, 1H), 3.88(s, 2H), 2.97–2.85(m, 1H), 2.76–2.65(m, 1H), 2.35(s, 3H), 2.34(s, 3H), 1.83–1.74(m, 2H).

The following compounds were obtained in accordance with the procedure of Example 22.

Example 103

1,2-Dimethyl-10-[3-(4-morpholino)propyl]phenothiazine-5-oxide

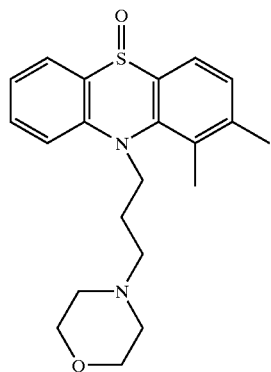

0.6 g of 1,2-dimethyl-10-(3-chloropropyl)phenothiazine-5-oxide obtained in Production Example 3, 260 ml of morpholine, a catalytic amount of triethylammonium iodide and 410 mg of potassium carbonate were added to 5 ml of N,N-dimethylformamide followed by stirring at 90° C. for 4 hr. Then the reaction mixture was cooled to room temperature. After adding water, the liquid reaction mixture was extracted with ethyl acetate. The organic layer was washed with brine and dried over anhydrous magnesium sulfate. After evaporating the solvent under reduced pressure, the residue was purified by silica gel column chromatography to give 430 mg of the title compound.

$^1$H-NMR, (400 MHz, CDCl$_3$) δ 7.78(m, 1H), 7.58(d, J=8, 1H), 7.52–7.49(m, 2H), 7.21–7.16(m, 1H), 7.13(d, J=8, 1H), 4.26(m, 1H), 4.08(m, 1H), 3.57(t, J=5, 4H), 2.39(s, 3H), 2.37(s, 3H), 2.32–2.15(m, 6H), 1.71(m, 2H).

The following compounds were obtained by the same procedure as the one of Example 103.

Example 130

1,2-Dimethyl-10-(3-cyanomethylpropyl)phenothiazine-5-oxide

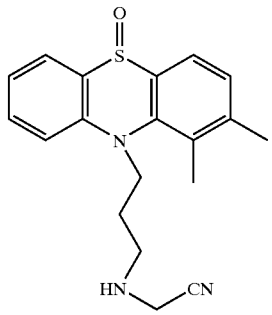

2.25 g of 1,2-dimethyl-10-(3-aminopropyl)phenothiazine-5-oxide synthesized in Example 8, 990 mg of bromoacetonitrile and 1.2 g of potassium carbonate were dissolved in 50 ml of N,N-dimethylformamide followed by stirring at 80° C. for 10 min. Then the reaction mixture was cooled to room temperature and, after adding water, extracted with ethyl acetate. The organic layer was washed with brine and dried over anhydrous magnesium sulfate. After evaporating the solvent under reduced pressure, the residue was purified by silica gel column chromatography to give 670 mg of the title compound.

$^1$H-NMR, (400 MHz, CDCl$_3$) δ 7.78(m, 1H), 7.58(d, J=8, 1H), 7.52–7.49(m, 2H), 7.21–7.16(m, 1H), 7.13(d, J=8, 1H), 4.36(m, 1H), 4.08(m, 1H), 3.39(s, 2H), 2.61(t, J=7, 2H), 2.37(s, 6H), 1.71(m, 2H).

The following compounds were obtained by the same procedure as the one of Example 130 or the same while changing the amount of the halide.

The following compounds were synthesized by treating the compound obtained by the same procedure as the one of Example 22 in the same manner as the one of Example 130.

Example 138

1,2-Dimethyl-10-[4-benzylamino(2-butenyl)]phenothiazine-5-oxide

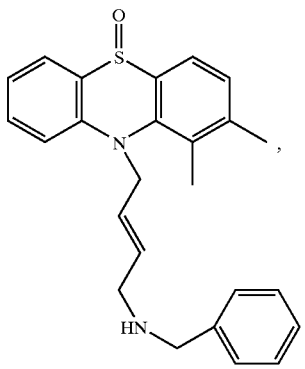

The procedure of Production Example 1 was repeated while using 1,4-dibromo-2-butene instead of 1-chloro-3-iodopropane followed by the procedure of Production Example 3. Then the procedure of Example 103 was repeated while using benzylamine instead of morpholine to give the title compound.

$^1$H-NMR, (400 MHz, CDCl$_3$) δ 7.72(d, J=8, 1H), 7.58–7.53(m, 2H), 7.49(d, J=8, 1H), 7.33–7.23(m, 5H), 7.20(t, J=8, 1H), 7.16(d, J=8, 1H), 5.68–5.63(m, 2H), 4.70 (dd, 14, 6, 1H), 4.48(dd, J=14, 6, 1H), 3.63(s, 2H), 3.13(d, J=4, 2H), 2.41(s, 3H), 2.39(s, 3H).

Example 139

1,2-Dimethyl-10-(3-benzylaminobutyl)phenothiazine-5-oxide

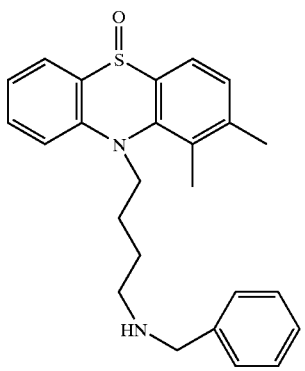

60 mg of 1,2-dimethyl-10-(4-benzylamino(2butenyl))phenothiazine-5-oxide obtained in Example 138 was dissolved in 10 ml of methanol. Then a catalytic amount of 10% palladium carbon was added thereto and the resulting mixture was stirred under hydrogen atmosphere of 1 atm for 2 hr. After filtering off the palladium carbon, the filtrate was concentrated and the residue was purified by silica gel column chromatography to give 10 mg of the title compound. $^1$H-NMR, (400 Hz, CDCl$_3$) δ 7.72(d, J =8, , 1H), 7.61–7.53(m, 2H), 7.49(d, J=8, 1H), 7.38–7.25(m, 5H), 7.19(t, J=8, 1H), 7.14(d, J=8, 1H), 4.42–4.30(m, 1H), 3.95–3.86(m, 1H), 3.83(d, J=12, 1H), 3.77(d, J=12, 1H), 2.56(t, J=7, 2H), 2.39(s, 3H), 2.36(s, 3H), 1.80–1.49(m, 4H)

The following compounds were obtained by the same procedure as that of Example 139 and Example 164 as will be described hereinbelow.

Example 142

1.2-Dimethyl-10-(2-aminoethyl)phenothiazine-5-oxide

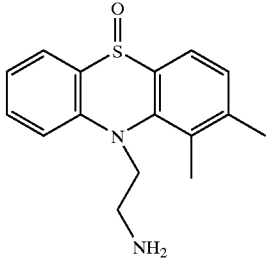

Starting with 1.95 g of 1,2-dimethyl-10-(2-phthalimidoethyl)phenothiazine obtained in Production Example 7, the procedures of Production Example 4 and Example 8 were repeated to give 1.24 g of the title compound. $^1$H-NMR, (400 MHz, CDCl$_3$) δ 7.81(dd, J=8, 1, 1H), 7.58(d, J=8, 1H), 7.56–7.49(m, 2H), 7.20(m, 1H), 7.13(d, J=8, 1H), 4.54(m, 1H), 4.18–4.09(m, 1H), 3.09–3.01(m, 1H), 2.75–2.50(m, 2H), 2.79(m, 1H), 2.38(s, 3H), 2.36(s, 3H).

Example 143

1.2-Dimethyl-10-(2-benzylaminoethyl)phenothiazine-5-oxide

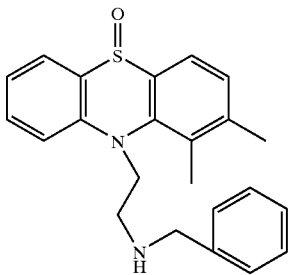

Starting with 600 mg of 1,2-dimethyl-10-(2-aminoethyl)phenothiazine-5-oxide obtained in Example 142, the procedure of Example 22 was repeated to give 755 mg of the title compound.

$^1$H-NMR, (400 MHz, CDCl$_3$) δ 7.81(dd, J=8, 1, 1H), 7.58(d, J=8, 1H), 7.54–7.45(m, 2H), 7.22–7.11(m, 7H), 4.50(m, 1H), 4.35–4.25(m, 1H), 3.59(s, 2H), 2.92(m, 1H), 2.66(m, 1H), 2.37(s, 3H), 2.36(s, 3H).

The following compounds were obtained by the same procedure as the one of Example 143.

Example 164

1,2-Dimethyl-10-[3-[N-[(2-hydroxyphenyl)methyl]methylamino]propyl]phenothiazine

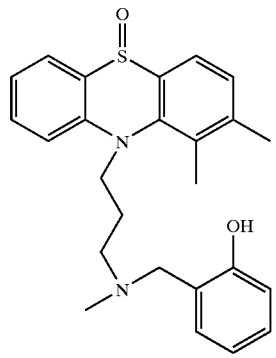

To 144 mg of 1,2-dimethyl-10-[3-[N-(2-hydroxyphenyl)methylamino]propyl]phenothiazine-5-oxide obtained by the same procedure as that of Example 22 were added 1 ml portions of formic acid and a 37% solution of formaldehyde followed by stirred under reflux for 3.5 hr. After adding water, the reaction mixture was basified by adding a saturated aqueous solution of sodium bicarbonate. Then it was extracted with methylene chloride and the organic layer was washed with a saturated aqueous solution and dried over sodium sulfate. After evaporating the solvent under reduced pressure, the residue was purified by silica gel column chromatography to give 120 mg of the title compound.

$^1$H-NMR, (400 MHz, CDCl$_3$) δ 7.79–7.77(m, 1H), 7.57 (d, J=8, 1H), 7.52–7.50(m, 2H), 7.21–7.12(m,3H), 6.89(dd, J=1, 8, 1H), 6.81(dd, J=1, 8, 1H), 6.77–6.73(m, 1H), 4.35–4.23(m, 11H), 4.02–3.94(m, 1H), 3.59 (d, J=14, 1H), 3.51 (d, J=14, 1H), 2.46–2.34(m, 2H), 2.39 (s, 3H), 2.37 (s, 3H), 2.11 (s, 3H), 1.84–1.75(m, 2H).

The following compounds were obtained by the same procedure as that of Example 164.

Example 191

1,2-Dimethyl-10-[2-(4-benzylpiperazin-1-yl)ethyl]-phenothiazine-5-oxide

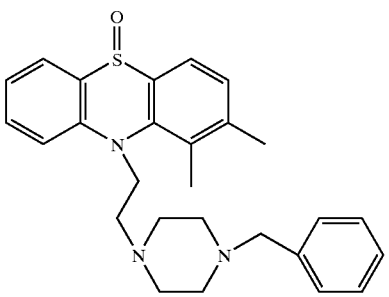

Starting with 1,2-dimethyl-10-(2-bromoethyl) phenothiazine obtained by Production Example 8, the procedures of Production Example 3 and Example 103 were repeated to thereby synthesize the title compound.

$^1$H-NMR, (400 MHz, CDCl$_3$) δ 7.78(d, J=8, 1H), 7.59(d, J=8, 1H), 7.41–7.48(m, 2H), 7.17–7.31(m, 6H), 7.14(d, J=8, 1H), 4.01–4.18(m, 2H), 3.42(s, 2H), 2.36(s, 3H), 2.34(s, 3H), 2.20–2.51(m, 10H).

The following compounds were obtained by the same procedure as that of Example 191.

Example 196

1,2-Dimethyl-10-(3-aminopropyl)phenothiazine-5,5-dioxide

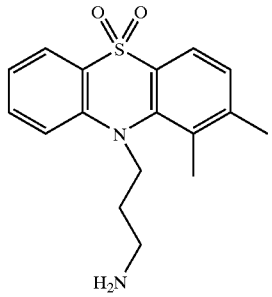

To 20 ml of a solution of 870 mg of 1,2-dimethyl-10-(3-aminopropyl)phenothiazine obtained in Example 1 in methanol was added an aqueous solution of 3.7 g of oxone in 20 ml of water and the resulting mixture was stirred at room temperature for 30 min. After evaporating the solvent, the residue was purified by silica gel column chromatography to give 200 mg of the title compound.

$^1$H-NMR, (400 MHz, CDCl$_3$) δ 7.96(dd, J=8, 1, 1H), 7.79(d, J=8, 1H), 7.57–7.53(m, 1H), 7.46(d, J=8, 1H), 7.24–7.20(m, 1H), 7.17(d, J=8, 1H), 4.15–4.10(m, 2H), 2.61(t, J=7, 2H), 2.38(s, 6H), 1.70–1.60(m, 2H).

The following compounds were obtained by subjecting the compounds obtained in Examples 1, 4, 8, 22 and 103 to the same procedures as those of Examples 196 and Production Example 3.

Example 203

3,4-Dimethyl-9-methylene-10-(3-ainopropyl)acridan

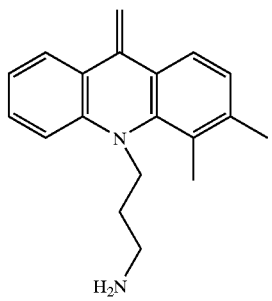

Starting with 154 mg of 3,4-dimethyl-9-methylene-10-(3-bromopropyl)acridan obtained by Production Example 9, the procedures of Production Example 2 and Example 1 were repeated to thereby give 87 mg of the title compound.

$^1$H-NMR, (400 MHz, CDCl$_3$) δ 7.52 (dd, J=8, 1, 1H), 7.31(d, J=7, 1H), 7, 24(dd, J=7, 1, 1H), 7.21(m, 1H), 7.01(m, 1H), 6.92(d, J=7, 1H), 5.36(s, 1H), 5.28(s, 1H), 3.85(t, J=7, 2H), 2.46(t, J=7, 2H), 2.30(s, 3H), 2.28(s, 3H), 1.54–1.43(m, 2H).

The following compounds were obtained by the same procedure as that of Example 203.

Example 206

3,4-Dimethyl-9-methylene-10-(3-benzylaminopropyl)acridan

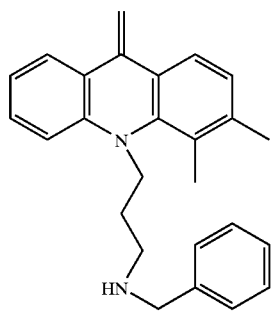

Starting with 100 mg of 3,4-dimethyl-9-methylene-10-(3-aminopropyl)acridan obtained by Example 203, the procedure of Example 22 was repeated to thereby give 45 mg of the title compound.

$^1$H-NMR, (400 MHz, CDCl$_3$) δ 7.53(dd, J=8, 1, 1H), 7.32(d, J=8, 1H), 7.28–7.17(m, 5H), 7.13–7.09(m, 2H), 7.01(m, 1H), 6.93(d, J=8, 1H), 5.35(s, 1H), 5.25(s, 1H), 3.87(t, J=7, 2H), 3.50(s, 2H), 2.36(t, J=7, 2H), 2.30(s, 3H), 2.28(s, 3H), 1.48(m, 2H).

The following compounds were obtained by the same procedure as that of Example 206.

Example 208

(E,Z)-3,4-Dimethyl-10-(3-aminopropyl)-9-acridoneoxime-O-methyl Ether

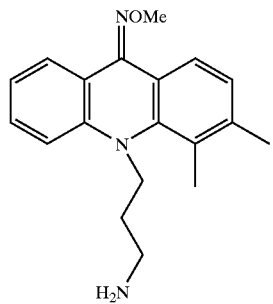

1 ml of hydrazine hydrate was added to a mixture of 480 mg of (E,Z)-3,4-dimethyl-10-(3-phthalimidopropyl)-9-acridoneoxime-O-methyl ether with 50 ml of methanol followed by stirring at room temperature for 1 hr. After evaporating the major part of methanol under reduced pressure, water was added to the residue followed by extraction with ethyl acetate. The organic layer was washed with brine and dried over anhydrous magnesium sulfate. After evaporating the solvent under reduced pressure, the residue was purified by silica gel column chromatography to give 260 mg of the title compound as a mixture of the E- and Z-enantiomers (1:1).

$^1$H-NMR, (400 MHz, CDCl$_3$) δ 8.42(dd, J=8, 2, 0.5H), 8.32(d, J=8, 0.5H), 7.80(dd, J=8, 2, 0.5H), 7.61(d, J=8, 0.5H), 7.39–6.96(m, 4H), 4.06(s, 1.5H), 4.05(s, 1.5H), 4.00–3.90(m, 2H), 2.41(t, J=7, 2H), 2.34(s, 1.5H), 2.33(s, 1.5H), 2.32(s, 1.5H), 2.31(s, 1.5H), 1.49–1.38(m, 2H).

The following compounds were synthesized by the same procedure as the one of Example 208.

Example 229

(E,Z)-3,4-Dimethyl-10-(3-benzylaminopropyl)-9-acridoneoxime-O-methyl Ether

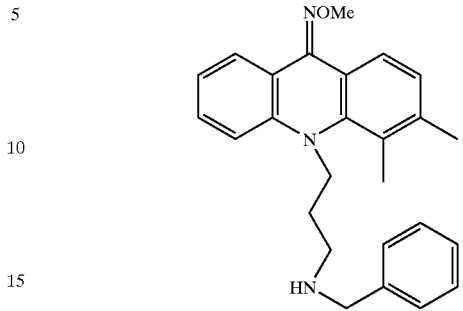

A mixture of 200 mg of (E,Z)-3,4-dimethyl-10-(3-aminopropyl)-9-acridoneoxime-O-methyl ether with 140 mg of benzaldehyde was stirred under reflux in 50 ml of ethanol. After cooling the mixture to room temperature, 200 mg of sodium borohydride was added thereto followed by stirring at room temperature for 10 min. After adding water, the reaction mixture was extracted with ethyl acetate. The organic layer was washed with brine and dried over anhydrous magnesium sulfate. After evaporating the solvent under reduced pressure, the residue was purified by silica gel column chromatography to give 180 mg of the title compound as a mixture of the E- and Z- enantiomers (1:1).

$^1$H-NMR, (400 MHz, CDCl$_3$) δ 8.43(dd, J=8, 2, 0.5H), 8.33(d, J=8, 0.5H), 7.81(dd, J=8, 2, 0.5H), 7.62(d, J=8, 0.5H), 7.38–6.96(m, 9H), 4.06(s, 1.5H), 4.05(s, 1.5H), 4.02–3.93(m, 2H), 3.50(s, 2H), 2.38–2.29(m, 8H), 1.55–1.45(m, 2H).

The following compounds were synthesized by the same procedure as the one of Example 229.

The following compounds were obtained by the same procedures as those of Production Examples 15, 2 and Example 1.

The following compounds were obtained by the same procedures as those of Production Examples 15, 2, Examples 1 and 22.

The following compounds were obtained by the same procedures as those of examples 22 and 164.

What is claimed is:

1. A nitrogen-containing tricyclic compound represented by the following formula (I), a hydrate thereof or a pharmacologically acceptable salt thereof:

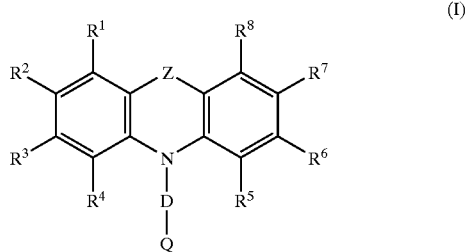

(I)

wherein $R^1$, $R^2$, $R^3$, $R^4$, $R^5$, $R^6$, $R^7$ and $R^8$ are the same or different from each other and each represents hydrogen, hydroxy, cyano, nitro, optionally substituted carbamoyl halogeno, optionally halogenated lower alkyl, optionally substituted cycloalkyl, optionally halogenated lower alkoxy, acyl, optionally protected carboxyl, optionally substituted aryl, optionally substituted heteroaryl, cycloalkylalkyl, hydroxylated alkyl, alkoxyalkyl, optionally protected carboxyalkyl, optionally substituted arylalkyl, optionally substituted heteroarylalkyl, cyanoalkyl, acylalkyl, optionally substituted carbamoylalkyl, optionally halogenated alkenyl, hydroxyalkenyl, alkoxyalkenyl, optionally protected carboxyalkenyl, optionally substituted arylalkenyl, optionally substituted heteroarylalkenyl, cyanoalkenyl, acylalkenyl, optionally substituted carbamoylalkenyl, optionally halogenated alkynyl, hydroxyalkynyl, alkoxyalkynyl, optionally protected carboxyalkynyl, optionally substituted arylalkynyl, optionally substituted heteroarylalkynyl, cyanoalkynyl, acylalkynyl, optionally substituted carbamoylalkynyl, hydroxyalkoxy, alkoxyalkoxy, optionally protected carboxyalkoxy, optionally substituted arylalkoxy, optionally substituted heteroarylalkoxy, —A—$NR^9R^{10}$, wherein A represents optionally substituted alkylene, optionally substituted alkenylene, optionally substituted alkynylene or a single bond; and $R^9$ and $R^{10}$ are the same or different from each other and each represents hydrogen, optionally halogenated lower alkyl, optionally substituted aryl or acyl, or $R^9$ and $R^{10}$ may form together with the nitrogen atom to which they are bonded a ring optionally having additional nitrogen, oxygen or sulfur, or

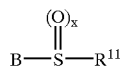

wherein B represents optionally substituted alkylene, optionally substituted alkenylene; optionally substituted alkynylene or a single bond; $R^{11}$ represents optionally halogenated lower alkyl or amino optionally substituted by lower alkyl; and x represents an integer of from 0 to 2;

provided that two of $R^1$, $R^2$, $R^3$, $R^4$, $R^5$, $R^6$, $R^7$, and $R^8$ adjacent to each other may form together with the carbon atom to which they are bonded a ring optionally containing oxygen, sulfur or nitrogen and optionally substituted;

Z represents

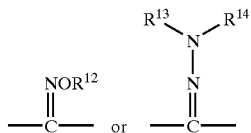

wherein $R^{12}$, $R^{13}$ and $R^{14}$ are the same or different from each other and each represents hydrogen, optionally substituted carbamoyl, optionally halogenated lower alkyl, optionally substituted cycloalkyl, acyl, optionally halogenated lower alkylsulfonyl, optionally substituted arylsulfonyl, optionally protected carboxyl, optionally substituted aryl, optionally substituted heteroaryl, cycloalkylalkyl, hydroxylated alkyl, alkoxyalkyl, optionally protected carboxyalkyl, optionally substituted arylakyl, optionally substituted heteroarylalkyl, cyanoalkyl, acylalkyl, optionally substituted carbamoylalkyl, optionally halogenated alkenyl, hydroxyalkenyl, alkoxyalkenyl, optionally protected carboxyalkenyl, optionally substituted arylalkenyl, optionally substituted heteroarylalkenyl, cyanoalkenyl, acylalkenyl, optionally substituted carbamoyalkenyl, optionally halogenated alkynyl, hydroxyalkynyl, alkoxyalkynyl, optionally protected carboxyalkynyl, optionally substituted arylalkynyl, optionally substituted heteroarylalkynyl, cyanoalkynyl, acylalkynyl, optionally substituted carbamoylalkynyl, —W—$NR^{18}R^{19}$, wherein W represents optionally branched alkylene, optionally branched alkenylene, optionally branched alkynylene or a single bond; $R^{18}$ and $R^{19}$ are the same or different from each other and each represents hydrogen, optionally halogenated lower alkyl or acyl, or $R^{18}$ and $R^{19}$ may form together with the nitrogen atom to which they are bonded a ring optionally containing additional nitrogen, oxygen or sulfur;

D represents optionally substituted alkylene, optionally substituted alkenylene, optionally substituted alkynylene or

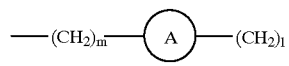

wherein m and l are each an integer of from 0 to 6; the ring A means an optionally substituted hydrocarbon ring or an optionally substituted heterocycle; and Q represents optionally substituted carbamoyl, acyl, acylalkyl, optionally protected carboxyl, optionally substituted heteroaryl, or —$NR^{20}R^{21}$, wherein $R^{20}$ and $R^{21}$ are the same or different from each other and each represents hydrogen, optionally halogenated lower alkyl, optionally halogenated lower alkoxy, hydroxylated alkyl, alkoxyalkyl, optionally substituted aryl, optionally substituted arylalkyl, optionally substituted heteroaryl, optionally substituted heteroarylalkyl, optionally substituted aryloxy, optionally substituted arylalkoxy, optionally substituted heteroaryloxy, optionally substituted heteroarylalkoxy, optionally protected carboxyalkyl, acyl, optionally substituted acylalkyl, optionally substituted acylamino, optionally substituted acylaminoalkyl, optionally substituted carbamoylalkyl, optionally substituted aminoalkyl, cyanoalkyl, acylalkyl, cycloalkyl, cycloalkylalkyl or amindino optionally substituted by lower alkyl, or $R^{20}$ and $R^{21}$ may form together with the nitrogen atom to which they are bonded an optionally substituted 3- to 8-membered ring which may have, as its ring-member other than carbon, at least one member selected from the group consisting of nitrogen, sulfur, oxygen and —$NR^{22}$, wherein $R^{22}$ represents hydrogen, optionally halogenated lower alkyl, acyl, optionally substituted acylalkyl, optionally substituted aryl, optionally substituted heteroaryl, optionally substituted arylalkyl, optionally substituted heteroarylalkyl or —$S(O)_s$—(Y)$_u$—$R^{23}$, wherein $R^{23}$ represents hydrogen, optionally halogenated lower alkyl or optionally substituted aryl; Y represents methylene; s is an integer of from 0 to 2; and u is 0 or 1, provided that the following compound is excluded:
the compound where $R^5$ and $R^6$ are both hydrogen atoms.

2. A nitrogen-containing tricyclic compound as set forth in claim 1, a hydrate thereof or a pharmacologically acceptable salt thereof, wherein neither $R^5$ nor $R^6$ is hydrogen.